(12) United States Patent
Rotondo et al.

(10) Patent No.: US 7,197,109 B2
(45) Date of Patent: Mar. 27, 2007

(54) REAL-TIME DIGITAL X-RAY IMAGING APPARATUS

(75) Inventors: Giuseppe Rotondo, Milan (IT); Marcello Molteni, Milan (IT); Costantino Nettis, Milan (IT)

(73) Assignee: Gendex Corporation, Washington, DC (US)

( * ) Notice: Subject to any disclaimer, the term of this patent is extended or adjusted under 35 U.S.C. 154(b) by 0 days.

(21) Appl. No.: 10/623,833

(22) Filed: Jul. 21, 2003

(65) Prior Publication Data

US 2004/0190678 A1    Sep. 30, 2004

Related U.S. Application Data

(60) Provisional application No. 60/398,436, filed on Jul. 25, 2002.

(51) Int. Cl.
*A61B 6/14* (2006.01)
(52) U.S. Cl. ......................... 378/39; 378/196
(58) Field of Classification Search ............ 378/38–40, 378/194, 195, 196–198, 20
See application file for complete search history.

(56) References Cited

U.S. PATENT DOCUMENTS

| 3,894,235 A | 7/1975 | Franke ................. 250/402 |
| 3,911,273 A | 10/1975 | Franke ................. 250/322 |
| 3,974,385 A | 8/1976 | Grim .................... 250/402 |
| 3,987,281 A | 10/1976 | Hodes ................. 235/151.3 |
| 3,991,314 A | 11/1976 | Schmitman et al. ...... 250/402 |
| 4,021,672 A | 5/1977 | Franke ................. 250/402 |
| 4,029,540 A | 6/1977 | Weidanz et al. ......... 156/522 |
| 4,061,920 A | 12/1977 | Möllendorf et al. ..... 250/413 |
| 4,070,578 A | 1/1978 | Timothy et al. ......... 250/336 |
| 4,097,741 A | 6/1978 | Pfeiler et al. .......... 250/322 |
| 4,104,531 A | 8/1978 | Weiss ................... 250/490 |
| 4,158,138 A | 6/1979 | Hellstrom .............. 250/402 |
| 4,160,906 A | 7/1979 | Daniels et al. .......... 250/322 |
| 4,160,997 A | 7/1979 | Schwartz ................ 358/93 |
| 4,188,537 A | 2/1980 | Franke .............. 250/416 TV |
| 4,241,254 A | 12/1980 | Valila |

(Continued)

FOREIGN PATENT DOCUMENTS

CA    1259711    9/1989

(Continued)

OTHER PUBLICATIONS

D.B. Forsyth et al. "Digital Imaging of Cephalometric Radiography, Part 1: Advantages and Limitations of Digital Imaging"; The Angle Orthodontist, vol. 66, No. 1, 1996; pp. 37-42.

(Continued)

*Primary Examiner*—Edward J. Glick
*Assistant Examiner*—Hoon Song
(74) *Attorney, Agent, or Firm*—McNees Wallace & Nurick LLC

(57) ABSTRACT

A x-ray diagnostic apparatus and methods perform Real-Time Digital Radiography with particular application in dental x-ray imaging modalities, such as Orthopantomography, Scannography, Linear Tomography and Cephalography, by using a versatile and robotized mechanical structure, featuring projection movements in the required a real range and automatic adaptation of the same mechanical structure to serve the various x-ray imaging modalities foreseen.

17 Claims, 19 Drawing Sheets

U.S. PATENT DOCUMENTS

| | | | |
|---|---|---|---|
| 4,247,780 A | 1/1981 | Webber et al. ............... 250/491 |
| 4,259,582 A | 3/1981 | Albert ........................ 250/402 |
| 4,352,987 A | 10/1982 | Hayashi et al. ............. 378/150 |
| 4,361,764 A | 11/1982 | Zieler ........................... 378/14 |
| 4,411,012 A | 10/1983 | Pfeiler et al. |
| 4,454,606 A | 6/1984 | Relihan ........................ 378/97 |
| 4,475,224 A | 10/1984 | Grassme ....................... 378/38 |
| 4,486,896 A | 12/1984 | Richter et al. .............. 378/108 |
| 4,495,632 A | 1/1985 | Nakano ........................ 378/40 |
| 4,501,010 A | 2/1985 | Grassme ....................... 378/38 |
| 4,521,899 A | 6/1985 | Finkenzeller et al. |
| 4,589,121 A | 5/1986 | Makino ........................ 378/39 |
| 4,603,427 A | 7/1986 | Alpern et al. |
| 4,641,331 A | 2/1987 | Makino et al. ............. 378/108 |
| 4,661,967 A | 4/1987 | Nishikawa |
| 4,675,888 A | 6/1987 | Gästrin ........................ 378/38 |
| 4,683,581 A | 7/1987 | Tammisalo et al. |
| 4,683,582 A | 7/1987 | Spolyar |
| 4,741,007 A | 4/1988 | Virta et al. ................... 378/39 |
| 4,783,793 A | 11/1988 | Virta et al. ................... 378/39 |
| 4,797,905 A | 1/1989 | Ochmann et al. ........... 378/108 |
| 4,811,372 A * | 3/1989 | Doebert et al. ............... 378/39 |
| 4,813,060 A | 3/1989 | Heubeck et al. ............. 378/39 |
| 4,815,115 A | 3/1989 | Nieminen et al. ........... 378/38 |
| 4,823,369 A | 4/1989 | Guenther et al. ............. 378/22 |
| 4,847,881 A | 7/1989 | Heubeck ...................... 378/38 |
| 4,856,038 A | 8/1989 | Guenther et al. ............. 378/39 |
| 4,878,234 A | 10/1989 | Pfeiffer et al. ................ 378/40 |
| 4,905,265 A | 2/1990 | Cox et al. ...................... 378/99 |
| 4,930,146 A | 5/1990 | Flakas et al. ............... 378/110 |
| 4,980,905 A | 12/1990 | Meccariello ................ 378/207 |
| 4,985,907 A | 1/1991 | Moteni ....................... 378/139 |
| 4,995,062 A | 2/1991 | Schulze-Ganzlin et al. ... 378/22 |
| 4,995,107 A | 2/1991 | Klingenbeck |
| 5,005,195 A | 4/1991 | Lanza et al. .................. 378/62 |
| 5,012,501 A | 4/1991 | Palonen et al. ............... 378/38 |
| 5,018,177 A | 5/1991 | McDavid et al. ............. 378/62 |
| 5,033,070 A | 7/1991 | Kanerva et al. |
| 5,043,582 A | 8/1991 | Cox et al. ............... 250/370.09 |
| 5,058,147 A | 10/1991 | Nishikawa et al. |
| 5,077,769 A | 12/1991 | Franciose ..................... 378/99 |
| 5,090,040 A | 2/1992 | Lanza et al. .................. 378/62 |
| 5,090,047 A | 2/1992 | Angotti et al. .............. 378/170 |
| 5,093,852 A | 3/1992 | Nishikawa et al. ........... 378/39 |
| 5,195,114 A | 3/1993 | Sairenji et al. ............... 378/40 |
| 5,214,686 A | 5/1993 | Webber ........................ 378/38 |
| 5,267,296 A | 11/1993 | Albert ........................ 378/113 |
| 5,293,312 A | 3/1994 | Waggener ............. 364/413.21 |
| 5,331,166 A | 7/1994 | Crosetto et al. ........ 250/370.11 |
| 5,355,398 A | 10/1994 | Nakano et al. ................ 378/39 |
| 5,386,448 A | 1/1995 | Tammisalo et al. ........... 378/38 |
| D355,964 S | 2/1995 | Nelvig ...................... D24/158 |
| 5,425,065 A | 6/1995 | Järvenin ....................... 378/40 |
| 5,434,418 A | 7/1995 | Schick .................. 250/370.11 |
| 5,454,022 A | 9/1995 | Lee et al. ................... 378/98.8 |
| 5,454,023 A | 9/1995 | Asikainen |
| 5,473,660 A | 12/1995 | Bastiaens et al. .......... 378/98.8 |
| 5,490,197 A | 2/1996 | Albert et al. ............... 378/113 |
| 5,506,879 A * | 4/1996 | Mori et al. .................... 378/39 |
| 5,511,106 A * | 4/1996 | Doebert et al. ............. 378/146 |
| 5,513,252 A | 4/1996 | Blaschka et al. .......... 378/98.8 |
| 5,519,437 A | 5/1996 | Nelvig ........................ 348/162 |
| 5,519,751 A | 5/1996 | Yamamoto et al. ........ 378/98.8 |
| 5,541,974 A | 7/1996 | Sklebitz .................... 378/98.8 |
| 5,579,361 A | 11/1996 | Augais et al. ................ 378/38 |
| 5,579,366 A | 11/1996 | Doebert et al. ............. 378/189 |
| 5,583,905 A | 12/1996 | Nishiki et al. ............. 378/98.8 |
| 5,590,167 A | 12/1996 | Arai ............................. 378/38 |
| 5,600,699 A | 2/1997 | Suzuki et al. ................. 378/38 |
| 5,602,896 A | 2/1997 | Diepstraten ................ 378/98.7 |
| 5,608,455 A | 3/1997 | Oda ........................... 348/245 |
| 5,617,462 A | 4/1997 | Spratt ........................ 378/98.7 |
| 5,625,662 A | 4/1997 | Toth et al. .................... 378/16 |
| 5,640,018 A | 6/1997 | Suzuki et al. ............... 250/368 |
| 5,663,998 A | 9/1997 | Suzuki et al. ................. 378/62 |
| 5,664,001 A | 9/1997 | Tachibana et al. ......... 378/98.8 |
| 5,668,375 A | 9/1997 | Petrick et al. .......... 250/370.09 |
| 5,677,940 A | 10/1997 | Suzuki et al. ................. 378/38 |
| 5,692,027 A | 11/1997 | Yoshimura et al. |
| 5,694,448 A | 12/1997 | Morcom .................... 378/98.8 |
| 5,708,503 A | 1/1998 | Carrieri |
| 5,742,659 A | 4/1998 | Atac et al. ................. 378/98.8 |
| 5,744,806 A | 4/1998 | Fröjd .................... 250/370.09 |
| 5,751,783 A | 5/1998 | Granfors et al. ............ 378/108 |
| 5,757,011 A | 5/1998 | Whitebook et al. .... 250/370.09 |
| 5,773,832 A | 6/1998 | Sayed et al. ........... 250/370.09 |
| 5,784,429 A | 7/1998 | Arai ............................. 378/38 |
| 5,793,837 A | 8/1998 | Mezhinsky et al. |
| 5,796,430 A | 8/1998 | Katoh et al. ................ 348/246 |
| 5,812,191 A | 9/1998 | Orava et al. ................ 348/308 |
| 5,828,720 A | 10/1998 | Syrjänen ...................... 378/38 |
| 5,828,721 A | 10/1998 | Schulze-Ganzlin et al. ... 378/38 |
| 5,864,146 A | 1/1999 | Karellas ..................... 250/581 |
| 5,878,104 A | 3/1999 | Ploetz |
| 5,887,049 A | 3/1999 | Fossum ..................... 378/98.8 |
| 5,892,227 A | 4/1999 | Schieber et al. ........ 250/370.12 |
| 5,912,942 A | 6/1999 | Schick et al. .............. 378/98.8 |
| 5,923,722 A | 7/1999 | Schulz ...................... 378/98.8 |
| 5,930,330 A | 7/1999 | Wolfe et al. ............... 378/98.2 |
| 5,933,471 A | 8/1999 | Kalvin ........................... 378/4 |
| 5,969,360 A | 10/1999 | Lee ....................... 250/370.09 |
| 5,974,166 A | 10/1999 | Ino et al. .................... 382/132 |
| 5,997,176 A * | 12/1999 | Fairleigh .................... 378/196 |
| 6,002,742 A | 12/1999 | Nelvig ...................... 378/98.8 |
| 6,035,013 A | 3/2000 | Orava et al. .................. 378/37 |
| 6,047,042 A | 4/2000 | Khutoryansky et al. ...... 378/62 |
| 6,055,292 A * | 4/2000 | Zeller et al. .................. 378/21 |
| 6,069,935 A | 5/2000 | Schick et al. .............. 378/98.8 |
| 6,081,739 A | 6/2000 | Lemchen .................... 600/407 |
| 6,093,019 A | 7/2000 | Morandi et al. ............. 433/29 |
| 6,094,467 A | 7/2000 | Gayer et al. .................... 378/4 |
| 6,118,842 A | 9/2000 | Arai et al. ..................... 378/39 |
| 6,169,780 B1 | 1/2001 | Yoshimura et al. ........... 378/39 |
| 6,173,035 B1 | 1/2001 | Tachibana et al. ............ 378/39 |
| 6,185,271 B1 | 2/2001 | Kinsinger |
| 6,208,706 B1 | 3/2001 | Campbell et al. ............... 378/9 |
| 6,243,439 B1 | 6/2001 | Arai et al. ..................... 378/20 |
| 6,289,074 B1 | 9/2001 | Arai et al. ...................... 378/4 |
| 6,325,537 B1 | 12/2001 | Watanabe |
| 6,351,519 B1 | 2/2002 | Bonk et al. ................. 378/98.8 |
| 6,385,279 B1 | 5/2002 | Toth et al. |
| 6,452,997 B1 | 9/2002 | Muller et al. |
| 6,466,641 B1 | 10/2002 | Virta et al. |
| 6,470,069 B1 | 10/2002 | Muller |
| 6,570,953 B1 * | 5/2003 | Dobert et al. ................. 378/21 |
| 6,731,717 B2 | 5/2004 | Kopsala |
| 6,829,326 B2 | 12/2004 | Woods |
| 6,891,921 B2 | 5/2005 | Kopsala |
| 7,092,483 B2 | 8/2006 | Nyholm |
| 7,103,141 B2 | 9/2006 | Sonobe et al. |

FOREIGN PATENT DOCUMENTS

| | | |
|---|---|---|
| DE | 42 38 268 | 5/1994 |
| DE | 44 33 545 | 3/1996 |
| DE | 196 48 076 | 5/1997 |
| DE | 196 48 052 | 6/1998 |
| DE | 197 54 463 | 6/1998 |
| DE | 197 31 927 | 2/1999 |
| DE | 197 34 717 | 2/1999 |
| EP | 0193650 A1 | 9/1986 |
| EP | 0 229 497 | 7/1987 |
| EP | 0 234 603 | 9/1987 |

| | | |
|---|---|---|
| EP | 0 279 294 | 8/1988 |
| EP | 0 373 717 | 6/1990 |
| EP | 0 415 075 | 3/1991 |
| EP | 0534 548 B1 | 3/1993 |
| EP | 0 632 994 | 1/1995 |
| EP | 0 632 995 | 1/1995 |
| EP | 0 634 671 | 1/1995 |
| EP | 0 408 167 | 9/1995 |
| EP | 0 673 623 | 9/1995 |
| EP | 0 685 201 | 12/1995 |
| EP | 0 574 368 | 4/1997 |
| EP | 0 776 124 | 5/1997 |
| EP | 0 776 149 | 5/1997 |
| EP | 0 784 965 | 7/1997 |
| EP | 0 858 773 | 8/1998 |
| EP | 0973047 A2 | 1/2000 |
| EP | 0 724 729 | 4/2000 |
| EP | 1 013 079 | 6/2001 |
| GB | 2304017 | 3/1997 |
| JP | 62 222 780 | 9/1987 |
| JP | 3 109 057 | 5/1991 |
| JP | 06000181 A | 1/1994 |
| WO | 89/07322 | 8/1989 |
| WO | 90/14793 | 12/1990 |
| WO | 91/15786 | 10/1991 |
| WO | 92/22188 | 12/1992 |
| WO | 93/00046 | 1/1993 |
| WO | 93/00649 | 1/1993 |
| WO | 93/11707 | 6/1993 |
| WO | 93/14418 | 7/1993 |
| WO | 93/23952 | 11/1993 |
| WO | 94/12855 | 6/1994 |
| WO | 96/32064 | 10/1996 |
| WO | 98/56214 | 12/1998 |
| WO | 99/08440 | 2/1999 |
| WO | 99/17659 | 4/1999 |
| WO | 99/62404 | 12/1999 |
| WO | 01/28298 | 4/2001 |
| WO | 01/66012 | 9/2001 |
| WO | 03/010556 | 2/2003 |

OTHER PUBLICATIONS

R.M. Harrison, "Digital Radiography"; Phys. Med. Biol., 1988, vol. 33, No. 7, pp. 751-784; Printed in the UK; IOP Publishing Ltd.

M.J. Yaffe and J.A. Rowlands; "X-Ray Detectors for Digital Radiography"; Phys. Med. Biol. 42 (1997), pp. 1-39; Printed in the UK; Imaging Research Program, Synnybrook Health Science Centre. The University of Toronto, Toronto, Ontario, Canada; PII: S0031-9155(97)36090-4; 1997 IOP Publishing Ltd.

Ann Wenzel and Hans-Goran Grondahl; "Direct Digital Radiography in the Dental Office"; International Dental Journal (1995) vol. 45, pp. 27-34; FDI/World Dental Press 1995.

William D. McDavid et al.; "Direct Digital Extraoral Radiography of the Head and Neck With a Solid-State Linear X-Ray Detector"; Dept. of Dental Diagnostic Science, University of Texas Health Science Center at San Antonio and Dept. of Oral Radiology, Karolinska Institute; Oral Surg. Oral Med Oral Pathol, Dec. 1992; vol. 74, No. 6, pp. 811-817.

A.R. Cowen et al.; "Direct Digital Mammography Image Acquisition"; Eur. Radiol. 7, pp. 918-930 (1997); Springer-Verlag 1997.

Y.J. Chen, S.K. Chen, H.F. Chang, K.C. Chen, "Comparison of Landmark Identification in Traditional Versus Computer-Aided Digital Cephalometry", The Angle Orthodontist, vol. 70, No. 5, pp. 384-392.

S. Dove, W.D. McDavid. "Digital Panoramic and Extraoral Imaging"; Dental Clinics of North America, Oct. 1998, vol. 37, No. 4, pp. 541-551.

D.B. Forsyth, W.C. Shaw, S. Richmond, C.T. Roberts, Digital Imaging of Cephalometric Radiographs, Part 2: Image Quality; The Angle Orthodontist, vol. 66, No. 1, 1996; pp. 43-50.

H. Visser, T. Rodig, K.P. Herman, "Dose Reduction by Direct-Digital Cephalometric Radiography"; The Angle Orthodontist, accepted Oct. 2000, 9 pages, vol. 71, No. 3, pp. 159-163.

* cited by examiner

REAL-TIME DIGITAL X-RAY IMAGING APPARATUS

BACKGROUND OF THE INVENTION

Orthopantomography, Scannography, Linear Tomography and Cephalography are complementary radiographic techniques, often combined in a single equipment, of widespread use in dental radiology to obtain respectively a comprehensive survey of the maxillo-facial complex, tomographic views of selected anatomical districts under transversal or axial projections, and cranial views under multiple projections, supporting the diagnosis in the dental prevention, restoration and follow up.

Orthopantomography aims to produce a radiographic image of a curved plane approximating the patient jaws, with blurring of the anatomical structures laying outside a narrow layer around the predesignated curved plane, by using the relative movement of the radiographic film versus the rotation of the x-ray source to generate the layer forming effect.

Scannography has a layer forming process similar to Orthopantomography, where the object is typically laying on a flat plane. It is practically used to produce axial or transverse views of specific anatomical districts, such as the jaw, the joints and the sinus.

Linear Tomography is an alternative technique, using the classic linear tomographic layer forming projection. It is practically used to produce axial or transverse views of specific anatomical districts in the jaw.

Cephalography is a stationary radiographic technique, aiming to produce radiographic images of the cranial complex under various projections, with minimum magnification and geometrical distortion.

For all the indicated radiographic modalities the real-time digital x-ray image acquisition is nowadays a more and more demanded feature. It provides instant image acquisition with reduced x-ray dosage, by taking advantage of the improved performances and reduced costs provided by the modem image imager technology. It also allows safer and cleaner operation, by removal of the film processing and related chemicals.

Both in conventional and digital modality, performing the radiographic techniques above typically requires a mechanical structure capable of performing orbital movements around the patient with simultaneous translation of the rotational centre.

A first difference is that in conventional Panoramic Radiography and Scannography the x-ray film is simultaneously translated at a speed such to obtain the blurring of the anatomical structures laying outside of the plane of interest, while in real time digital applications the x-ray film is replaced by the x-ray imager and special electronic techniques are used to produce the same blurring effect.

A second difference is that in conventional Cephalography and Linear Tomography a stationary x-ray film is used, while in real-time digital applications the stationary x-ray film can be replaced by a stationary x-ray imager.

Alternatively, to significantly reduce the system cost, a linearly shaped x-ray imager will be preferably used, and the image acquisition will be performed by using a horizontal or vertical scanning technique.

Another important difference is that, due to the high cost of the x-ray imager, in real-time digital applications it will be very desirable to have an apparatus and method to relocate the x-ray imager, either manually or automatically, from the Panoramic to the Cephalographic position.

The fundamental concept on which this invention is based was described in prior art application (U.S. Pat. No. 4,985,907), where the roto-translatory system is disclosed realized by two independent translations movements in a plane and one independent rotation movement about an axis perpendicular to that plane. The present invention further expands this concept, by disclosing the new apparatuses and methods required for the real-time digital implementation of the indicated radiographic modalities.

Other prior art (U.S. Pat. No. 4,741,007) describes apparatus and methods in which the roto-translatory movement is realised by means of two pivot shafts placed at a constant distance from each other, using a guide groove and an active actuator.

Further prior art (U.S. Pat. No. 5,012,501) describes apparatus and methods in which a variety of orbital movements is produced by using a first drive for the rotational movement, a second drive for the linear translation of the rotation centre, and a selector for selecting the direction of the linear motion.

More recent prior art (WO 99/17659) describes apparatus and methods in which pivot shafts connecting multiple body parts are driven by active actuators in a SCARA arrangement, allowing a variety of projection movements as required for various dental x-ray imaging modalities.

The concept of the three independent roto-translatory movements disclosed in prior art (U.S. Pat. No. 4,985,907) has proven its flexibility in producing multiple orbital projections by simple adjustment of the software programming data, and can be advantageously used for the generation of the orbital movements required for Orthopantomography, Scannography, and Linear Tomography, both in Conventional and Real-Time Digital Radiography.

The main difference will be that in Real-Time Digital Radiography the film cassette with its independent drive is removed, and is replaced by the x-ray imager having an active area of a size equivalent to the x-ray field at the film plane as used in Conventional Radiography.

However, it will be the purpose of this invention to further exploit the basic concept in order to implement the following desirable features:

Perform Real-Time Digital Cephalography by means of horizontal, vertical or rotatory scanning movements, allowing at the same time ergonomic and reproducible immobilisation of the patient by suitable positioning system.

Perform automatic relocation of the x-ray imager between the Panoramic and Cephalographic positions, in order to allow use of the same imager in both imaging modalities.

SUMMARY OF THE INVENTION

The object of the invention is a x-ray apparatus providing a robotized mechanical structure capable of performing Real-time Digital Radiography with particular application in Orthopantomography, Scannography, Linear Tomography and Cephalography.

In Real-Time Digital Orthopantomography, Scannography and Linear Tomography the apparatus of the invention will be based on the fundamental robotic concept disclosed in U.S. Pat. No. 4,985,907, with the difference that the film cassette with its independent drive will be removed, and the x-ray imager will be introduced.

Various kinds of x-ray imagers will be allowed, and the active area of the x-ray imager will be of a size equivalent to the x-ray field at the film plane as used in Conventional Radiography.

In Real-Time Digital Cephalography a first approach may be to replace the conventional radiographic film by a x-ray imager of equivalent size.

Also in this case various kinds of x-ray imagers used, based on existing technologies well known to those skilled in the art, such as CCD or CMOS or Amorphous Silicon readout devices optically coupled with scintillator screens or electrically coupled with direct x-ray detection screens.

This approach may become convenient in the future, but is very expensive at the present status of technology and does not offer today an economic solution for the dental practice application.

The alternative approach for Real-Time Digital Cephalography is to implement the radiographic image acquisition by a scanning movement, either in the horizontal or vertical direction, or rotatory.

It will allow use of a linear shaped x-ray imager with reduced active area, so offering a cost effective solution for the implementation of the Real-Time Digital Cephalography.

The robotic solution shall be usefully complemented by a mechanism performing automatic relocation of the x-ray imager between the Panoramic and Cephalographic positions.

The purpose is to allow in a simple and effective way the use of the same x-ray imager in all the foreseen imaging modalities, with evident positive impact on the overall system cost.

An innovative approach for Real-Time Digital Cephalography is also illustrated, where the same rotating arm conventionally used for panoramic technique is translated according to a predefined path in order to project from a virtual rotating centre the linear shaped sensor and build up, by using a geometric correction software algorithm, the cephalographic image acquisition by a scanning movement.

The invention is particularly advantageous in dental radiography, where the outlined features find immediate application, but it could also be advantageously employed in other medical and non-medical applications having similar requirements.

Here following is a description in greater detail of the invention, based on the exemplary embodiment illustrated in the attached drawings.

DESCRIPTION OF DRAWINGS AND TABLES

FIGS. 7, 7a, 7b, and 7c are diagrams of different embodiments of the present invention for vertical scanning movement of the x-ray source and the primary x-ray collimator.

Figure 8:
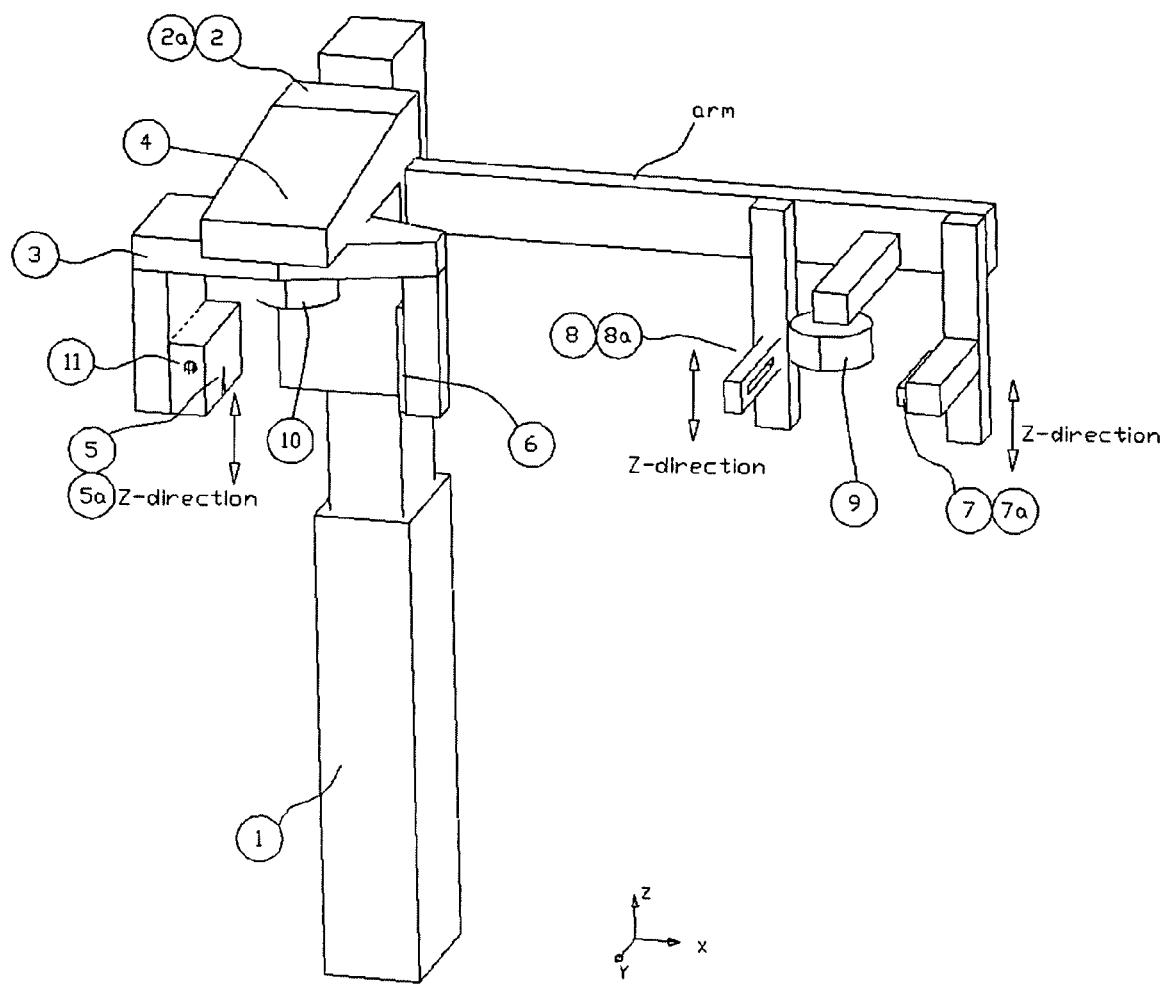
Figure 8A:
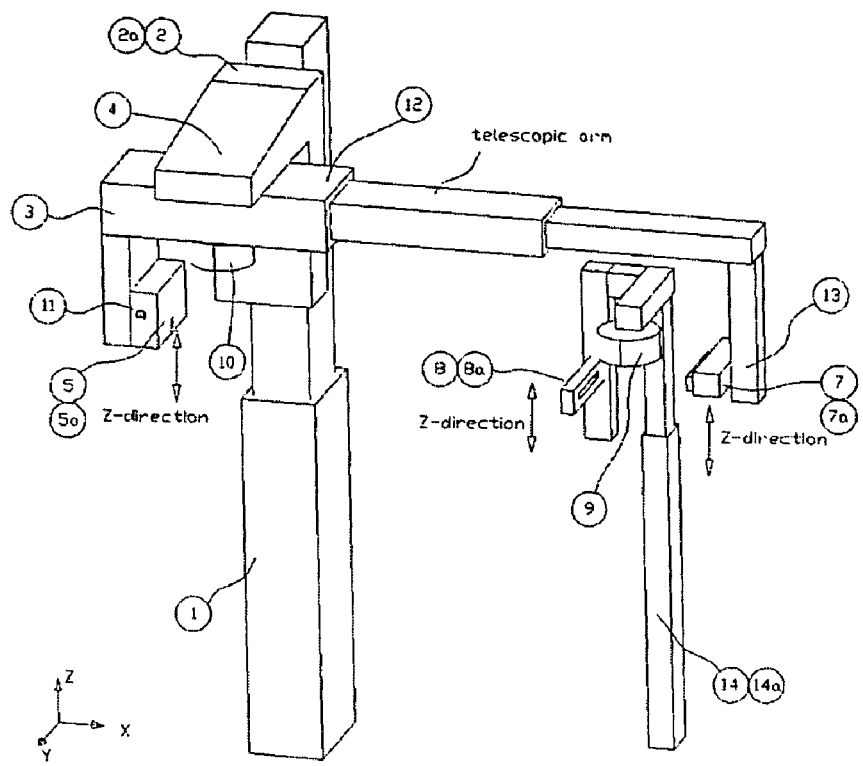
Figure 8B:
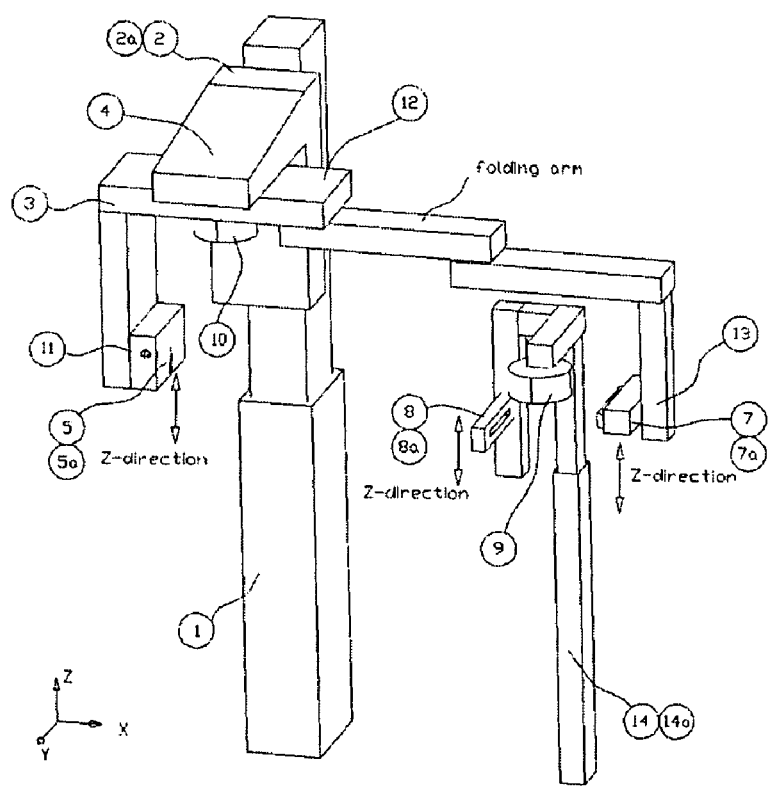

FIGS. 8, 8a, and 8b are diagrams of different embodiments of the present invention for vertical scanning movement of the primary x-ray collimator.

FIGS. 9, 9a, 9b, 9C and 9D are diagrams of different embodiments of the present invention for rotational scanning movement of the primary x-ray collimator.

Wherever possible, the same reference numbers will be used throughout the drawings to refer to the same or like parts.

Figure 10:
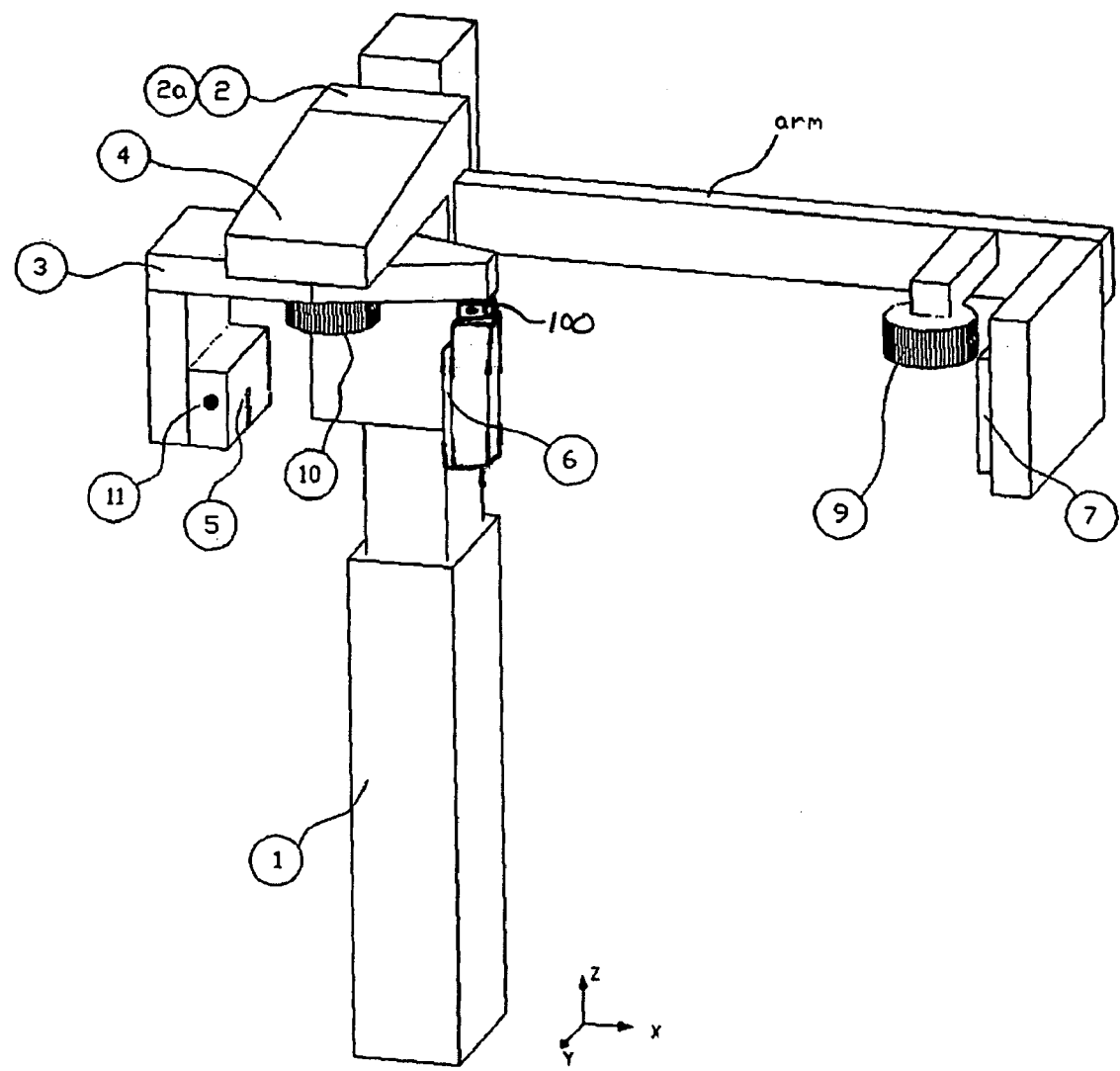

FIG. 10 is a diagram of an embodiment of the present invention illustrating a detachable connector for the x-ray imager.

DETAILED DESCRIPTION

The system is a representative dental x-ray diagnostic system performing Real-time Digital Radiography in Orthopantomography, Scannography, Linear Tomography and Cephalography.

For those skilled in the art, it is intended that:

Orthopantomography is a narrow beam scanning technique aiming to reproduce in a single radiographic view the whole or part of a curve plane approximating the patient jaw, using layer forming methods by which the points laying in the target plane are reproduced on the same point of the radiographic image, while points laying outside the target plane are blurred out.

Scannography is a narrow beam scanning technique aiming to reproduce in a single radiographic view the whole or part of a flat plane approximating specific anatomical regions (such as the jaw, the joints, the sinus), using layer forming methods by which the points laying in the target plane are reproduced on the same point of the radiographic image, while points laying outside the target plane are blurred out.

Linear tomography is a wider beam radiographic technique, using the classic linear tomographic layer forming projection, where by the combined movement of x-ray source and x-ray imager around the object, only the points laying in the target plane are reproduced on the same point of the radiographic image, while points laying outside the target plane are blurred out.

Cephalography is a stationary radiographic technique, where the cranial complex is exposed under various projections, with minimum magnification and geometrical distortion.

The apparatus of the invention is based on the robotic concept already disclosed in U.S. Pat. No. 4,985,907, with the difference that the film cassette with its independent drive is removed, and the x-ray imager is introduced.

Additionally it proposes various arrangements for performing Real-Time Digital Cephalography either by a single large area x-ray imager, or by horizontal, vertical or rotational scanning with a linear shaped x-ray imager.

Finally it describes suitable mechanisms for the automatic relocation of the x-ray imager from Panoramic to Cephalographic positions.

Figure 1:
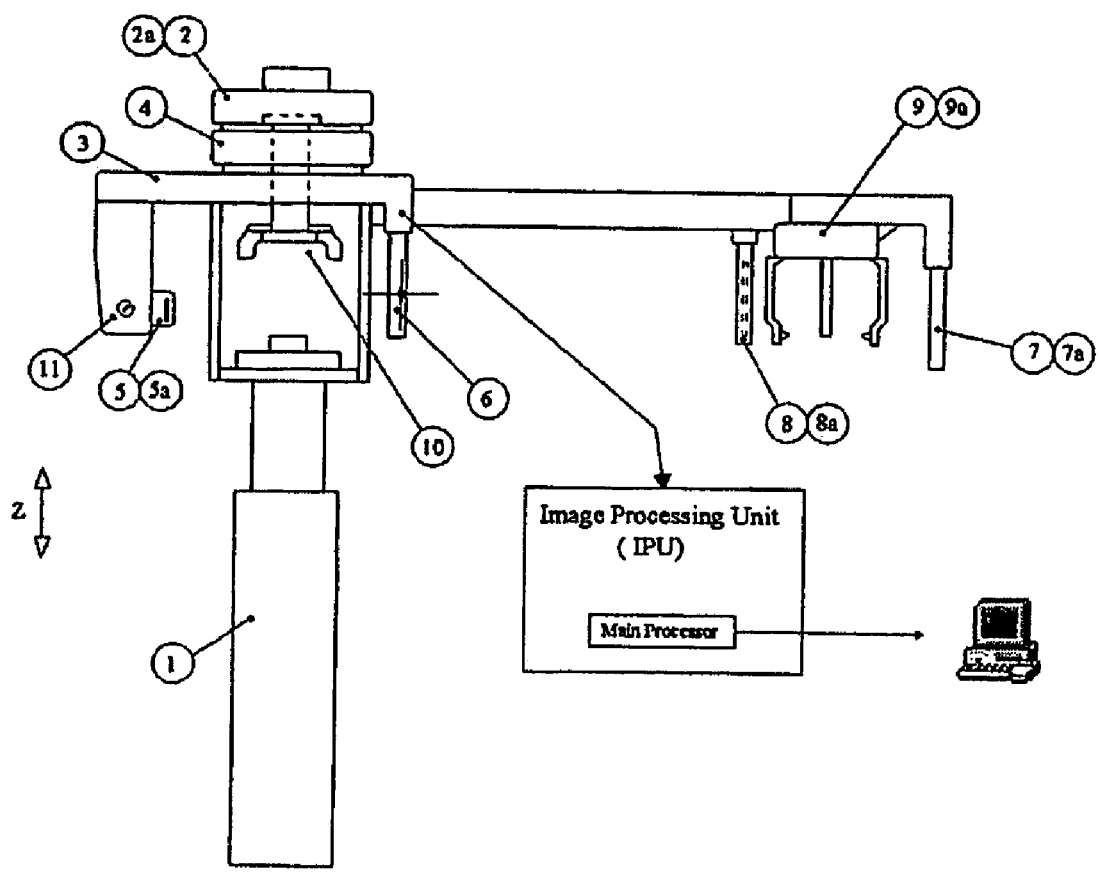
FIG. 1 is a diagram showing an exemplary system dedicated to dental applications.

FIG. 1 illustrates the most general arrangement of the system and its main mechanical and electrical components.

The base 1 supports the whole apparatus. Frame 2 slides vertically along the base and is provided with an independent drive 2a for the control of the vertical movement. The vertical movement is used during patient positioning, for the vertical adjustment to the patient height, and may also be used for vertical scanning in the relevant Cephalographic arrangement.

The rotary unit 3 is connected to the Frame 2 by the Cinematic Assembly 4. It supports the x-ray source 11 at one end, and the x-ray imager 6 at the other end.

The x-ray imager 6 is dedicated to the image acquisition in Panoramic Radiography, Scannography and Linear Tomography.

The x-ray source 11 provides the x-ray generation and includes the x-ray tube and the focal spot from which the x-ray beam generates.

A primary x-ray collimator 5 is attached to the output port of the x-ray source 11, providing limitation of the radiation incident on the x-ray imagers.

Preferably the x-ray collimator will be of the motorised type, operated by the independent active actuator 5a under micro computer control.

The x-ray imager 7 is dedicated to the image acquisition in Cephalography. It is rigidly attached, by an arm or the like, to the frame 2. Alternatively it may be attached to the rotary frame 3, in case that the configurations adopting automatic sensor relocation as later described are used.

The x-ray imager is also provided with an independent active actuator 7a, to be used in configurations where the linear movement of the same x-ray imager is required during a scanning process, as later described.

A secondary x-ray collimator 8 is attached to frame 2. Alternatively it may be attached to the rotary frame 3 or to an independent support, in cases where configurations adopting automatic sensor relocation as later described are used.

It is provided with an actuator 8a driving the movement of the same collimator aligned with the x-ray beam during a scanning process under micro computer control, as later described.

The actuator 8a may be independent or mechanically controlled by the actuator 7a of the x-ray imager.

A first patient positioning system 10 rigidly attached to the frame 2 is provided for Panoramic Radiography, Scannography and Linear Tomography, while a second patient positioning system 9, also rigidly attached to the frame 2, is provided for Cephalography.

In alternative arrangements, where the scanning process is used, the patient positioning system 9 used in Cephalography may be independently attached either to the base frame 1, or to the floor, or to the wall, and be provided with an independent actuator, either active or not, for the adjustment to the patient height.

In other alternative arrangements, where the automatic sensor relocation is used as explained later, the patient positioning system 9 used in Cephalography may be attached to the rotary frame 3, and be provided with an independent active actuator 9a, allowing its repositioning relative to its support frame in order to maintain a firm patient position during a horizontal or vertical scanning process where the movement of the same support frame is involved.

Figure 2:
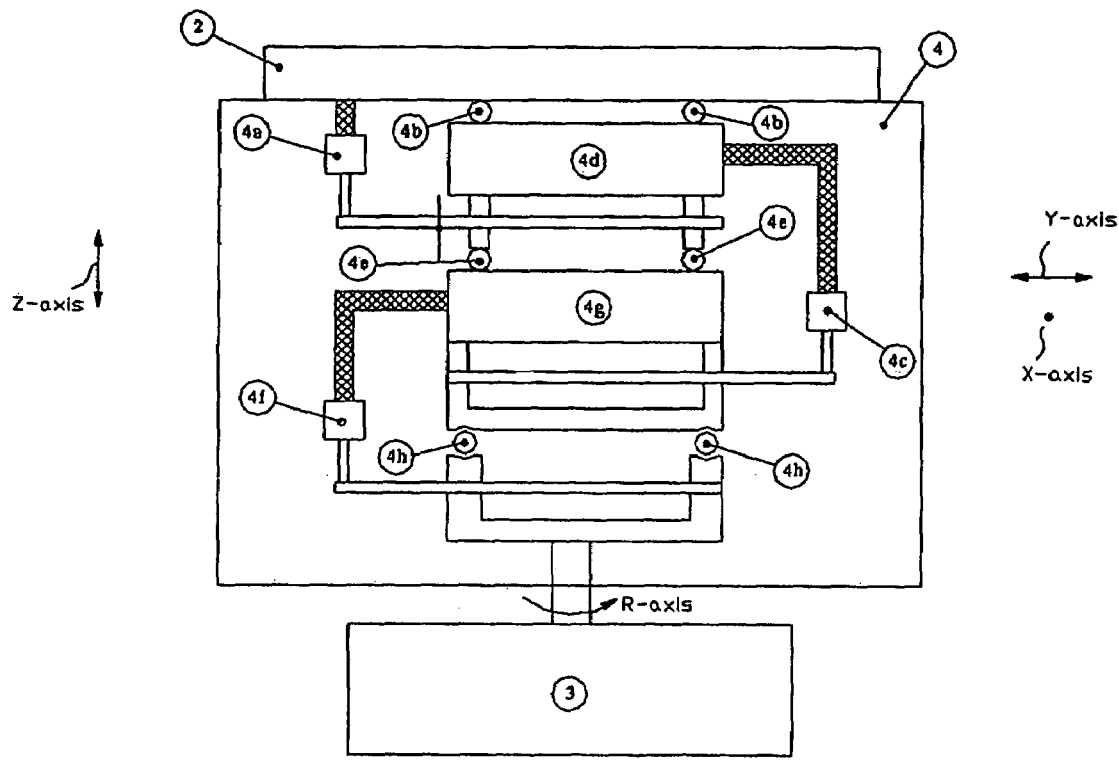
FIG. 2 is a block diagram of the Cinematic Assembly system.
Figure 2:
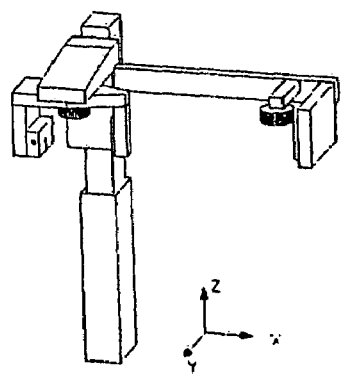

FIG. 2 illustrates the detail of the Cinematic Assembly 4.

The Cinematic Assembly 4 implements the robotic concept, by providing 3 independent axis for the rotation R, the X linear movement, and the Y linear movement.

The X linear axis is composed by the motor drive 4a rigidly connected to the frame 2, and the linear bearing 4b.

The Y linear axis is composed by the motor drive 4c rigidly connected to the support 4d, and the linear bearing 4e.

The R (rotation) axis is composed by the motor drive 4f rigidly connected to the support 4g, and the circular bearing 4h.

The x-ray imagers 6 and 7 can be of various kinds according to the state of the art.

The x-ray imager assembly construction will be based on existing technologies, and will typically consist of one or more sensor devices, each providing a detector modality, optically or electrically coupled to a readout device.

The detection modality can be a scintillating screen converting x-rays into light, hence requiring optical coupling to the readout device, or it can be other direct detector materials (such as CdTe, CdZnTe, HPGe, $HgI_2$, GaAs, $PbI_2$) providing direct conversion of x-rays to electric charge, hence requiring electrical bonding to the readout device pixels.

The readout layer is a semiconductor device whose fabrication is based on various available technologies, among which CCD, CMOS or Amorphous Silicon, well known to those skilled in the art.

Figure 3:
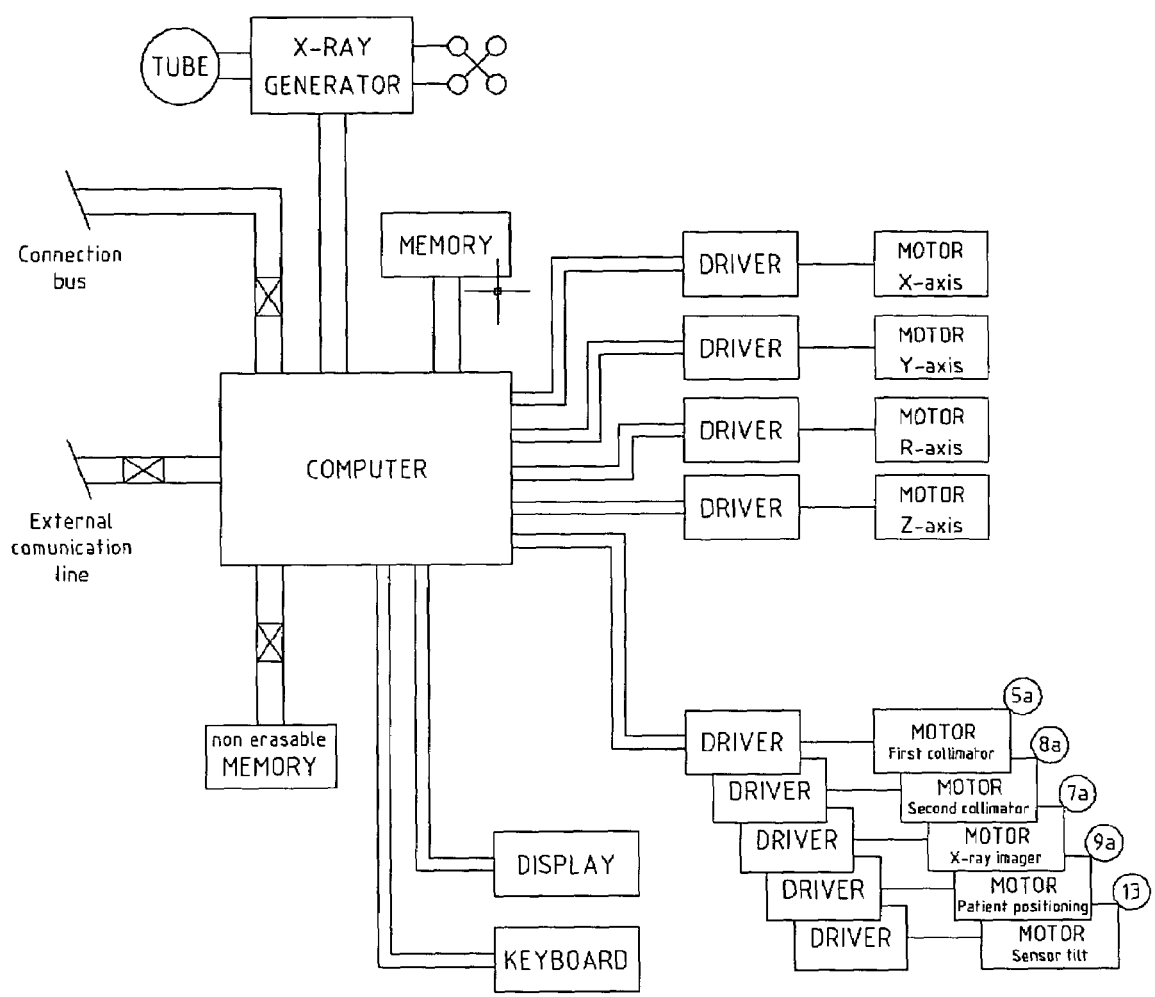
FIG. 3 is a schematic diagram of a control system for the present invention.

FIG. 3 shows a scheme for the control system for an apparatus according to the invention.

One or more microcontrollers 16 and associated memory 17 form the system micro computer, feeding the independent motor drives X,Y,R with cinematic profiles data associated to the specific orbital projection.

It also controls the actuator 7a associated with the x-ray imager 7, the actuator 5a associated with the primary x-ray collimator 5, the actuator 8a associated with the secondary x-ray collimator 8, the actuator 9a associated with the patient positioning system, and the actuator 2a associated with the vertical slide of frame 2, for the movements required during the normal operation and during the various scanning processes foreseen in Cephalography.

Figure 4:
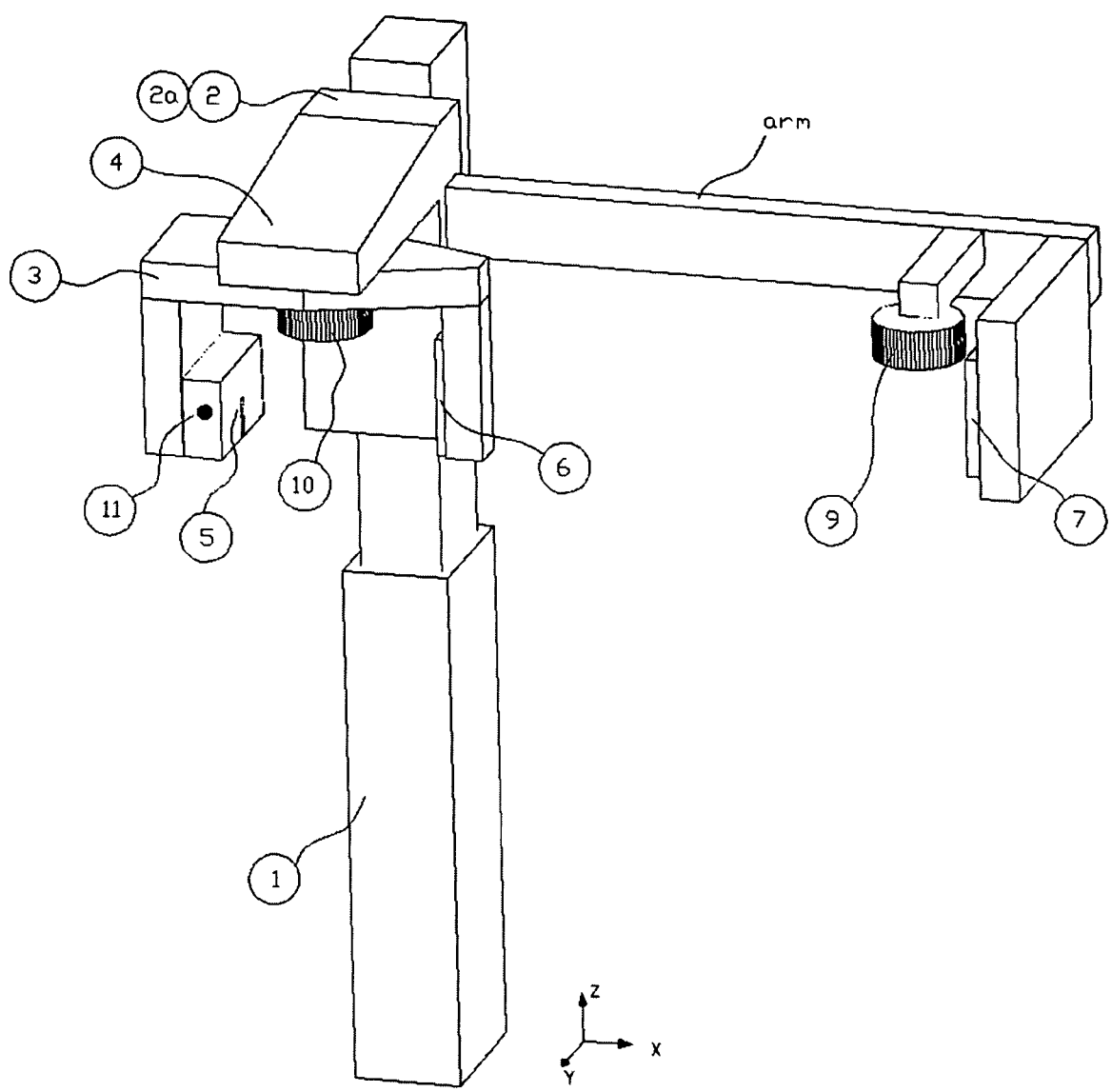
FIGS. 4, 4a and 4b are diagrams of different embodiments of the present invention substituting an x-ray imager for conventional radiographic film.
Figure 4A:
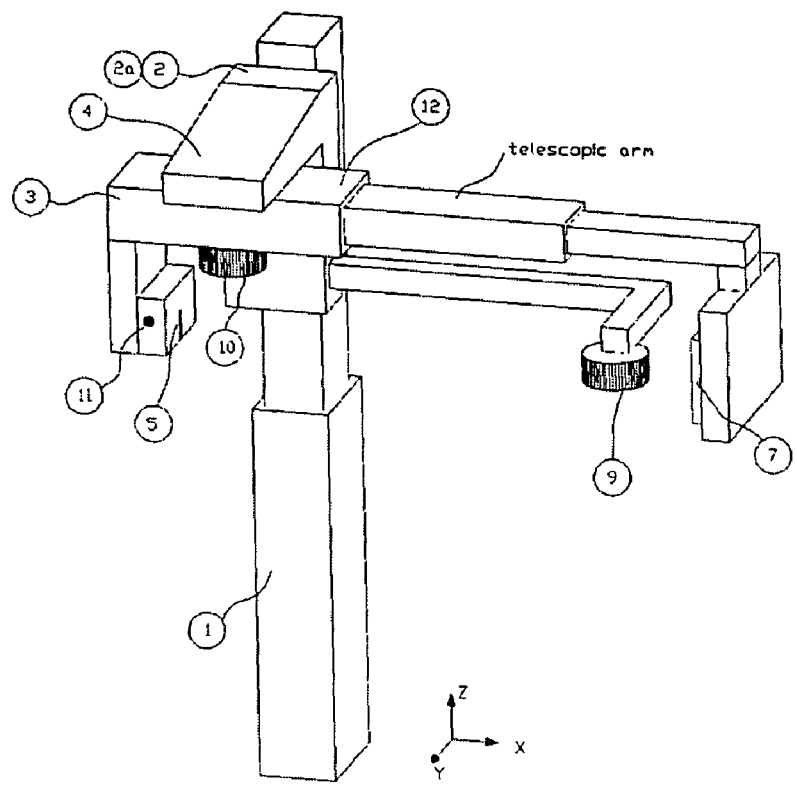
Figure 4B:
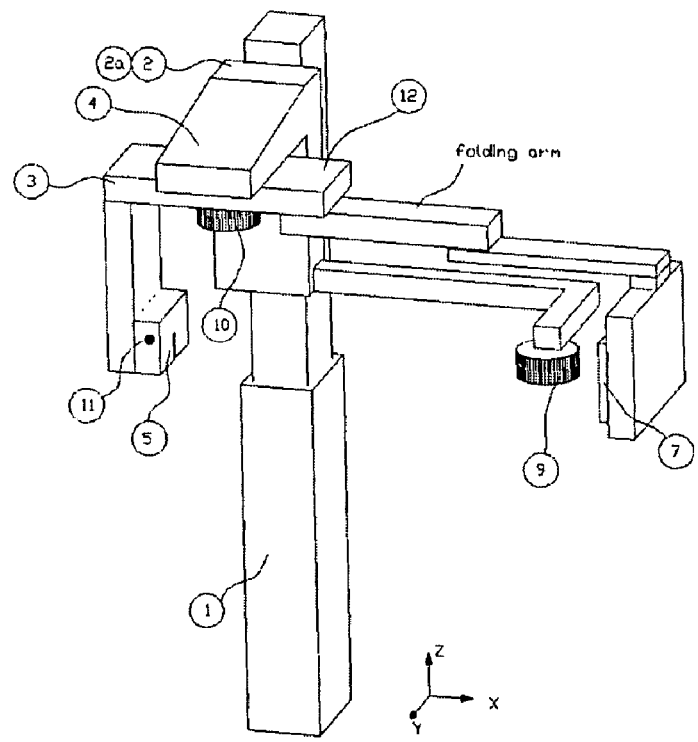

In FIG. 4, 4a, 4b arrangements are shown where the Real-Time Digital Cephalography is implemented by replacing the conventional radiographic film by a x-ray imager 7 of equivalent size.

In all the arrangements the primary x-ray collimator 5 is kept steady, and there is no secondary collimator.

In FIG. 4 is a first arrangement where the Cephalographic patient positioning system 9 is supported on the same arm where the x-ray imager is suspended. The arm is rigidly connected to the frame 2.

In the alternative arrangements of FIG. 4a, 4b, a single large area x-ray imager can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

In FIG. 4a an arrangement is illustrated, where the x-ray imager 7 is relocated from Cephalographic to Panoramic position and vice versa by using a telescopic arm, either provided with an active actuator 12 or to be manually actuated.

The Cephalographic patient positioning system 9 is supported on a separate arm rigidly connected to the frame 2.

In FIG. 4b another arrangement is illustrated, where the x-ray imager 7 is relocated from Cephalographic to Panoramic position and vice versa by using a folding arm, either provided with an active actuator 12 or to be manually actuated.

The Cephalographic patient positioning system 9 is also supported on a separate arm rigidly connected to the frame 2.

In FIG. 5, 5a, 5b, 5C, 5D arrangements are shown where the Real-Time Digital Cephalography is implemented by a scanning process in the horizontal direction achieved by a movement of the x-ray source 11, using a narrow x-ray beam and a linear shaped x-ray imager having an active area of a length approximately corresponding to the minimum useful height of the x-ray field size at the film plane used in Conventional Cephalography.

In these arrangements software post-processing of the acquired image will be required to correct the magnification distortions in the Y direction.

Figure 5:
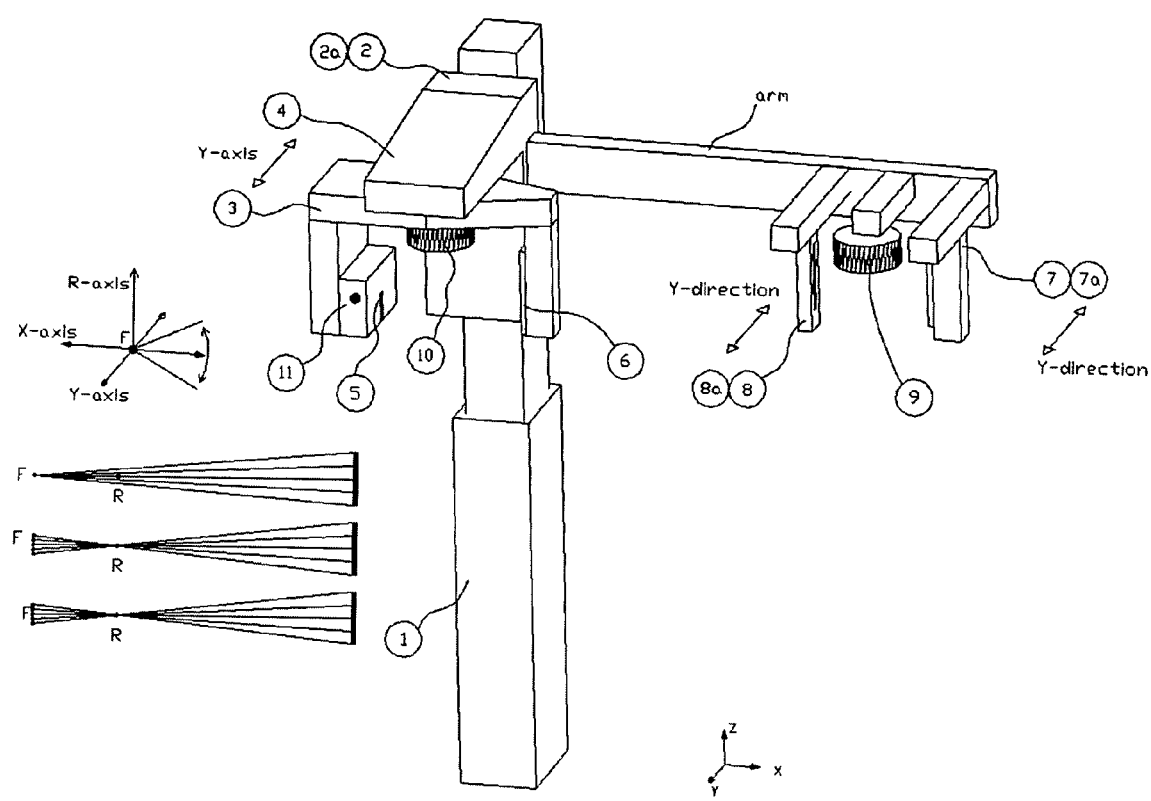
FIGS. 5, 5a, 5b, 5C and 5D are diagrams of different embodiments of the present invention for horizontal scanning movement of the x-ray source and the primary x-ray collimator.

In FIG. 5 a first arrangement is illustrated where the x-ray source 11 and the primary x-ray collimator 5 are simultaneously and linearly moved in the Y direction, by acting on the Y axis under microcomputer control during the scanning sequence.

The secondary x-ray collimator 8 and the x-ray imager 7 are synchronously moved, aligned with the x-ray beam, by using the respective drive axis, 8a and 7a, under microcomputer control during the horizontal scanning sequence.

The Cephalographic patient positioning system 9 is supported on the same arm where the x-ray imager is suspended. The arm is rigidly connected to the frame 2.

In this arrangement there are several other alternative movements of the x-ray source 11 which can advantageously used to realize the scanning process. By utilizing the roto-translating capabilities of the cinematic unit, the x-ray source 11 can perform a rotational movement around its focal point, otherwise it can move along a trajectory characterized in having a constant distance between the focal point and the x-ray sensor, otherwise more generally it can perform a projection from a predefined virtual centre of rotation.

Still referring to FIG. 5, arrangements are here following illustrated where the Real-Time Digital Cephalography is implemented by a scanning process in the horizontal direction achieved by a roto-translating movement of the x-ray source 11, using a narrow x-ray beam and the same linear shaped x-ray imager 6 used for Panoramic Radiography, Scannography and Linear Tomography.

In such case the active area of the x-ray imager may require an additional length in order to cover all the anatomical regions of interest.

In a first arrangement the rotary frame 3 performs a linear trajectory in the Y direction, by acting on the Y axis under microcomputer control during the scanning sequence.

In other more complex arrangements, by utilizing the roto-translating capabilities of the cinematic unit, the rotary frame 3 can perform roto-translating scanning trajectories where the object is illuminated from a predefined virtual centre of irradiation among which those depicted in FIG. 5.

In all these arrangements software post-processing of the acquired image will be required to perform geometric correction of the magnification distortions.

In the alternative arrangements of FIG. 5a, 5b, 5C, 5D, the x-ray imager 7 can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

Figure 5A:
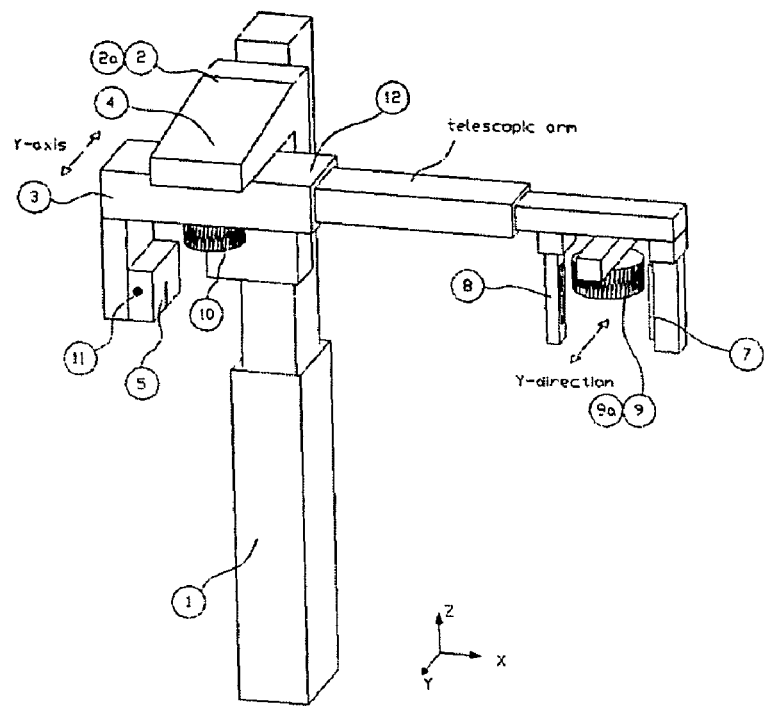

In FIG. 5a an arrangement is illustrated where the x-ray source 11, the primary collimator 5, the secondary collimator 8, and the x-ray imager 7 are simultaneously and linearly moved in the Y direction, by acting on the Y axis under microcomputer control during the scanning sequence.

The Cephalographic patient positioning system 9 is supported on the same arm where the x-ray imager is suspended, while an independent active actuator 9a shall be foreseen providing movement relative to the support arm in opposition to the scanning movement under microcomputer control, in order to maintain the patient in a firm position.

The x-ray imager 7 can be relocated from Cephalographic to Panoramic position and vice versa by using a telescopic arm either provided with an active actuator 12 or to be manually actuated.

Figure 5B:
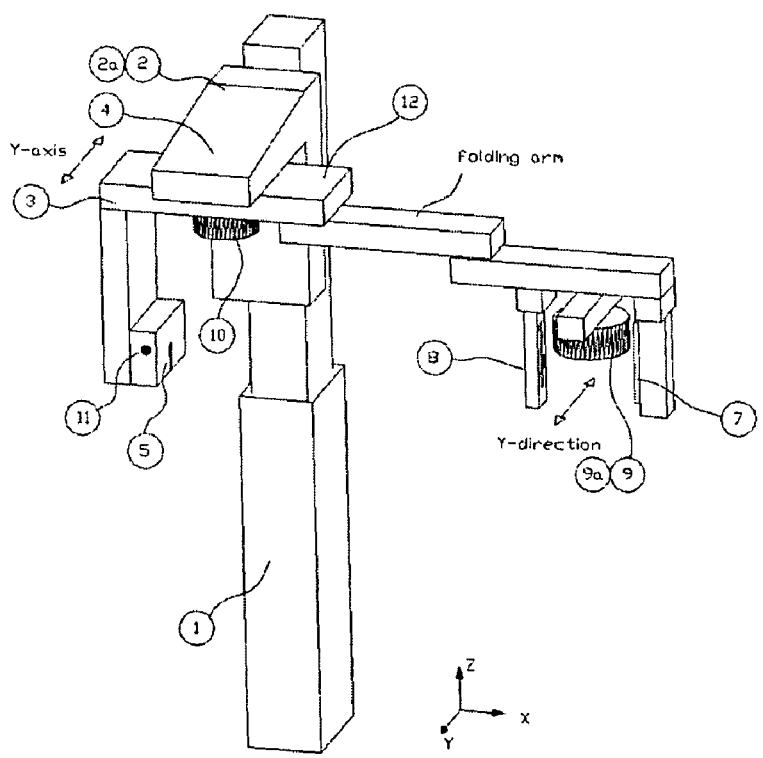

In FIG. 5b an arrangement is illustrated where the x-ray source 11, the primary collimator 5, the secondary collimator 8, and the x-ray imager 7 are simultaneously and linearly moved in the Y direction, by acting on the Y axis under microcomputer control during the scanning sequence.

The Cephalographic patient positioning system 9 is supported on the same arm where the x-ray imager is suspended, while an independent active actuator 9a shall be foreseen providing movement relative to the support arm in opposition to the scanning movement under microcomputer control, in order to maintain the patient in a firm position.

The x-ray imager 7 can be relocated from Cephalographic to Panoramic position and vice versa by using a folding arm either provided with an active actuator 12 or to be manually actuated.

Figure 5C:
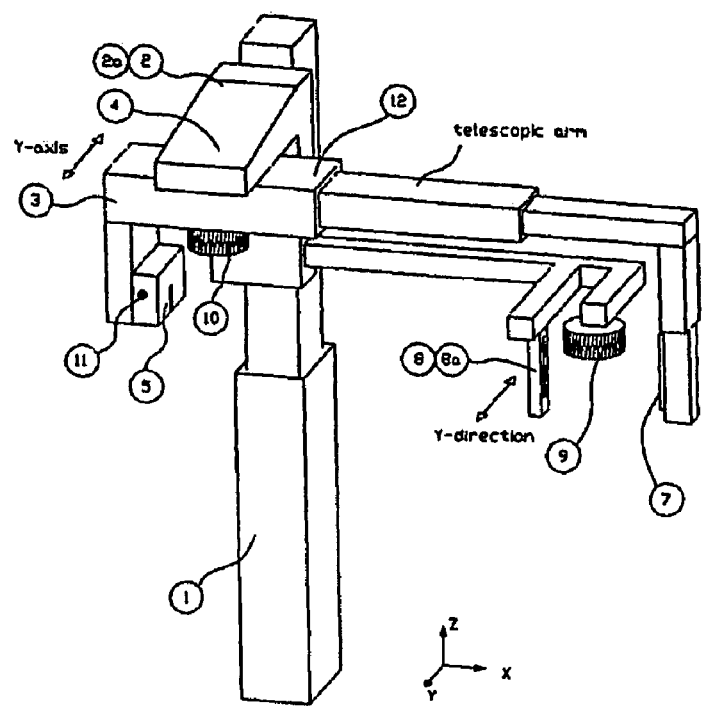

In FIG. 5C an arrangement is illustrated where the x-ray source 11, the primary collimator 5, and the x-ray imager 7 are simultaneously and linearly moved in the Y direction, by acting on the Y axis under microcomputer control during the scanning sequence.

The secondary x-ray collimator 8 is synchronously moved by its actuator 8a and kept aligned with the x-ray beam under microcomputer control during the scanning process.

The Cephalographic patient positioning system 9 is kept steady during the scanning process, supported by an arm rigidly connected to the frame 2.

The x-ray imager 7 can be relocated from Cephalographic to Panoramic position and vice versa by using a telescopic arm either provided with an active actuator 12 or to be manually actuated.

Figure 5D:
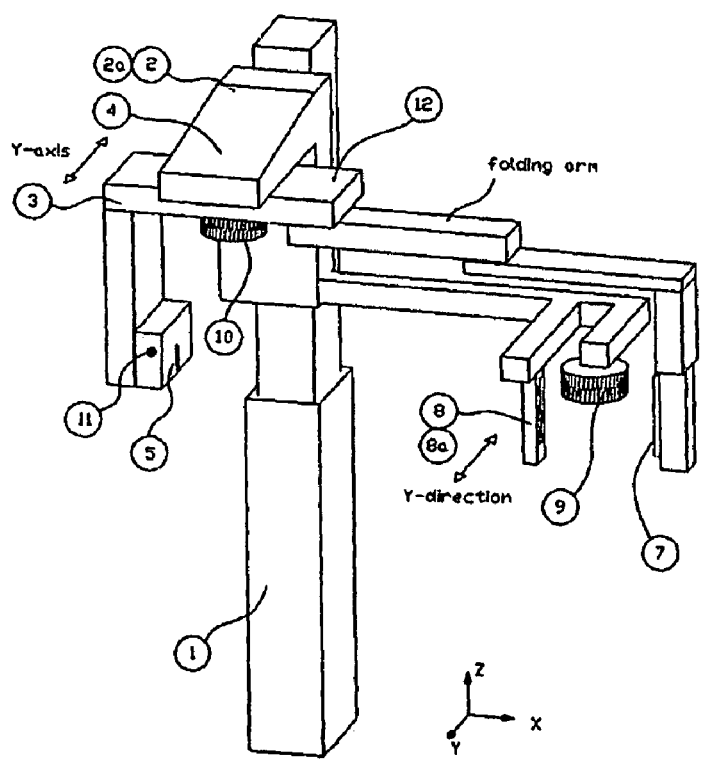

In FIG. 5D an arrangement is illustrated where the x-ray source 11, the primary collimator 5, and the x-ray imager 7 are moved linearly in the Y direction, by acting on the Y axis under microcomputer control during the scanning sequence.

The secondary x-ray collimator 8 is synchronously moved by its actuator 8a and kept aligned with the x-ray beam under microcomputer control during the scanning process.

The Cephalographic patient positioning system 9 is kept steady during the scanning process, supported by an arm rigidly connected to the frame 2.

The x-ray imager 7 is relocated from Cephalographic to Panoramic position and vice versa by using a folding arm either provided with an active actuator 12 or to be manually actuated.

In FIG. 6, 6a, 6b, 6C, 6D arrangements are shown where the Real-Time Digital Cephalography is implemented by a scanning movement in the horizontal direction of the primary x-ray collimator 5, using a narrow x-ray beam and a linear shaped x-ray imager having an active area of a length approximately corresponding to the minimum useful height of the x-ray field size at the film plane used in Conventional Cephalography.

In this case no software post-processing of the acquired image will be required.

Figure 6:
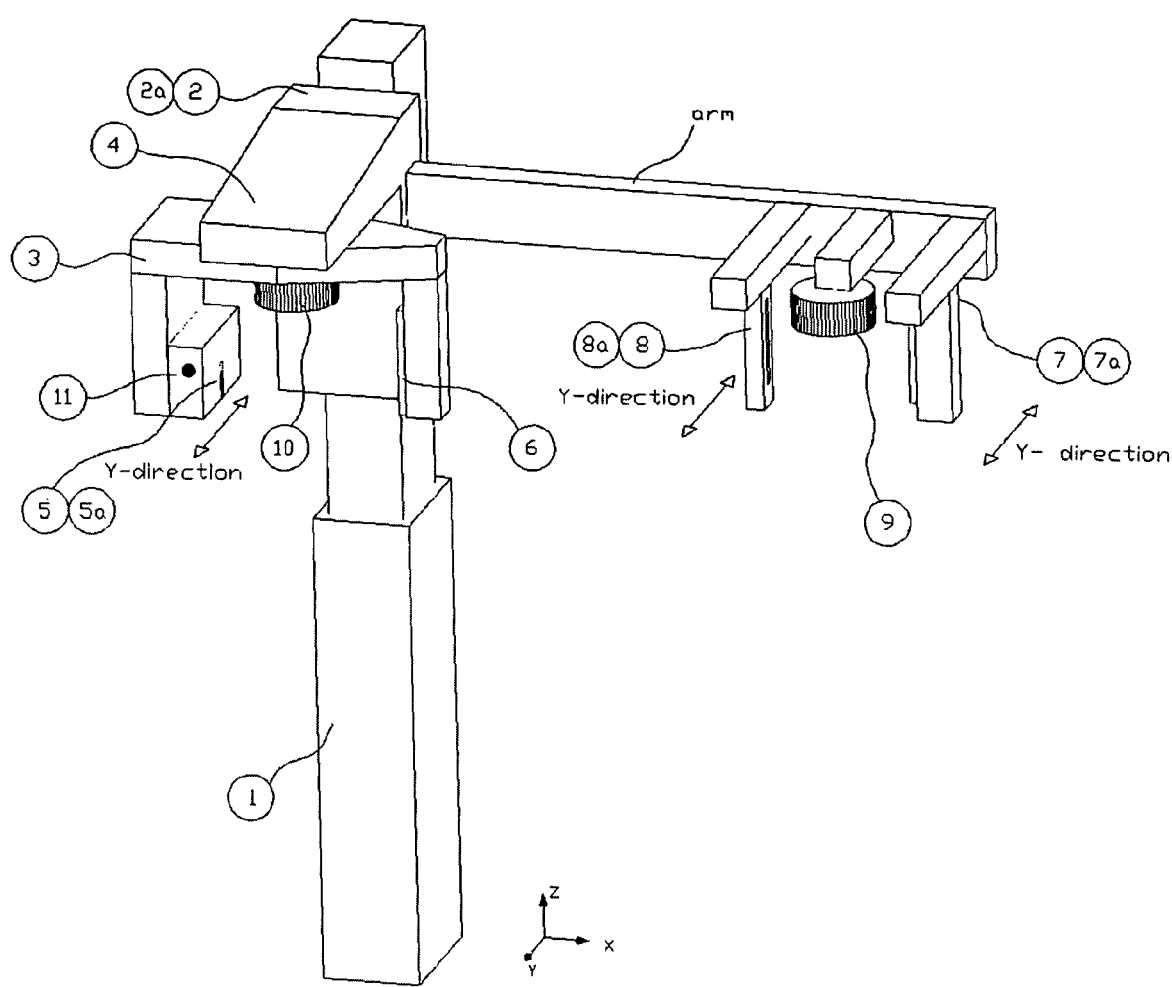
FIGS. 6, 6a, 6b, 6C and 6D are diagrams of different embodiments of the present invention for horizontal scanning movement of the primary x-ray collimator.

In FIG. 6 an arrangement is illustrated where the x-ray source 11 is kept steady, while the primary x-ray collimator 5, the secondary x-ray collimator 8 and the x-ray imager 7 are synchronously moved, aligned with the x-ray beam, by using the respective drive axis under microcomputer control during the horizontal scanning sequence.

The Cephalographic patient positioning system 9 is supported on the same arm where the x-ray imager is suspended. The arm is rigidly connected to the frame 2.

In the alternative arrangements of FIG. 6a, 6b, 6C, 6D, the x-ray imager 7 can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

Figure 6A:
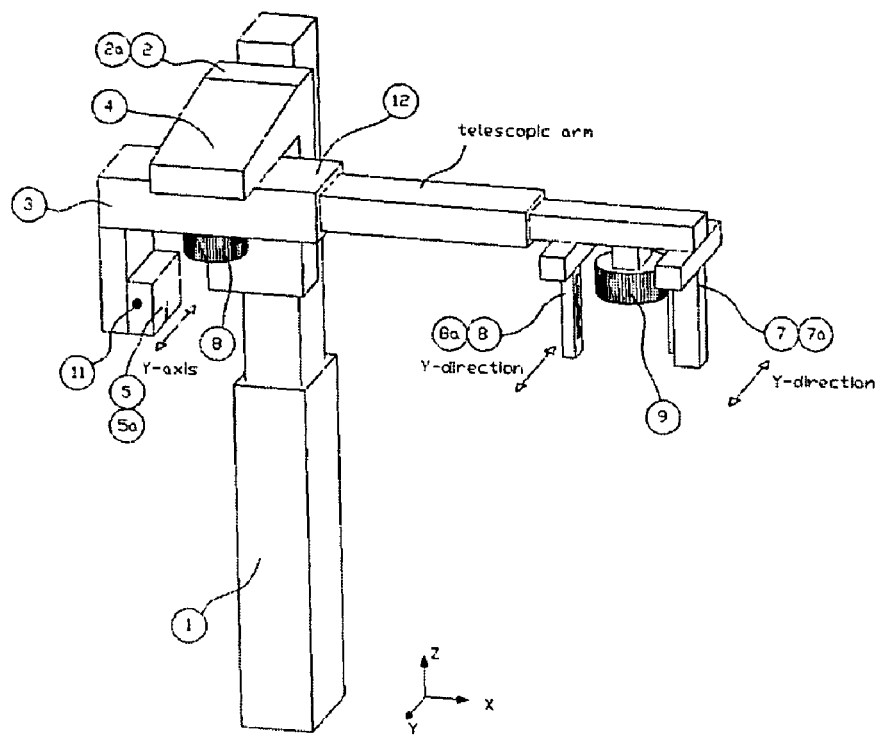

In FIG. 6a an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a and 7a, under microcomputer control during the horizontal scanning sequence.

The Cephalographic patient positioning system 9 is supported on the same arm where the x-ray imager 7 is suspended and is kept steady during the scanning process.

The x-ray imager 7 can be relocated from Cephalographic to Panoramic position and vice versa by using a telescopic arm either provided with an active actuator 12 or to be manually actuated.

Figure 6B:
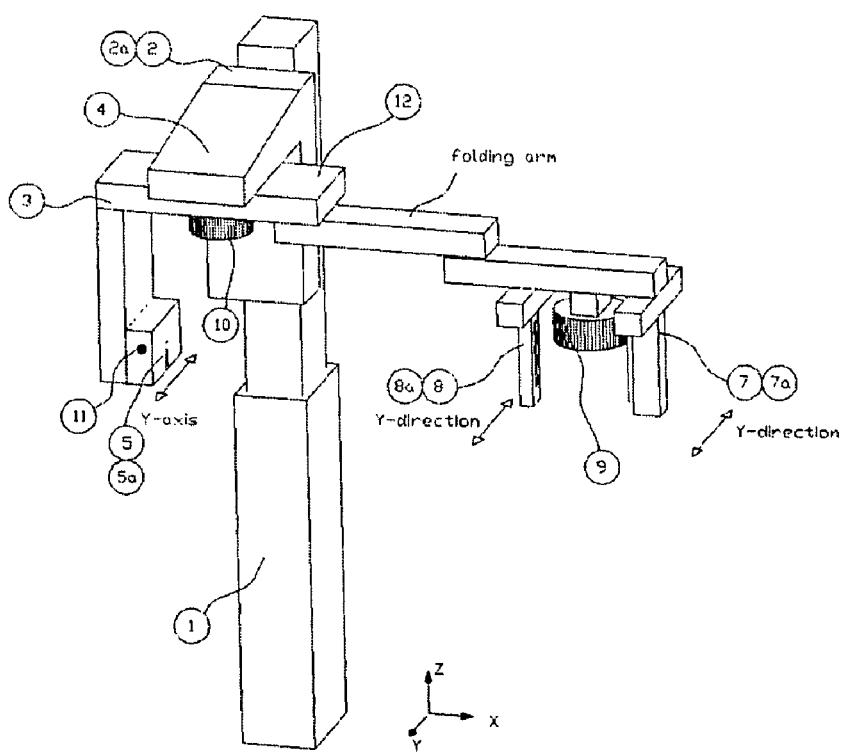

In FIG. 6b an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a and 7a, under microcomputer control during the horizontal scanning sequence.

The Cephalographic patient positioning system 9 is supported on the same arm where the x-ray imager is suspended and is kept steady during the scanning process.

The x-ray imager 7 can be relocated from Cephalographic to Panoramic position and vice versa by using a folding arm either provided with an active actuator 12 or to be manually actuated.

Figure 6C:
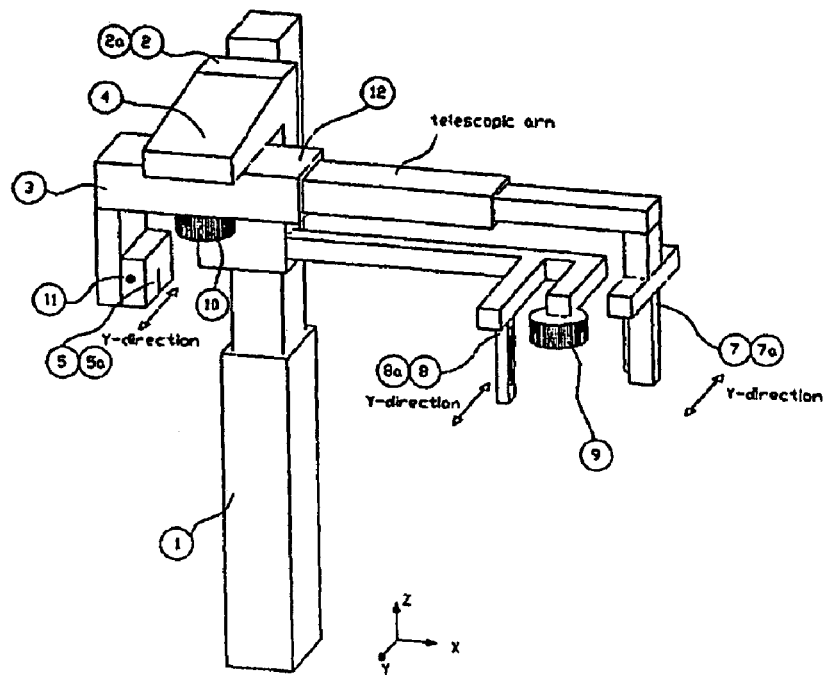

In FIG. 6C an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a, and 7a, under microcomputer control during the horizontal scanning sequence.

The secondary x-ray collimator 8 and the Cephalographic patient positioning system 9 are supported on an arm rigidly connected to the frame 2. The independent actuator 8a shall be foreseen providing movement of the secondary collimator 8 relative to the arm.

The x-ray imager 7 can be relocated from Cephalographic to Panoramic position and vice versa by using a telescopic arm either provided with an active actuator 12 or to be manually actuated.

Figure 6D:
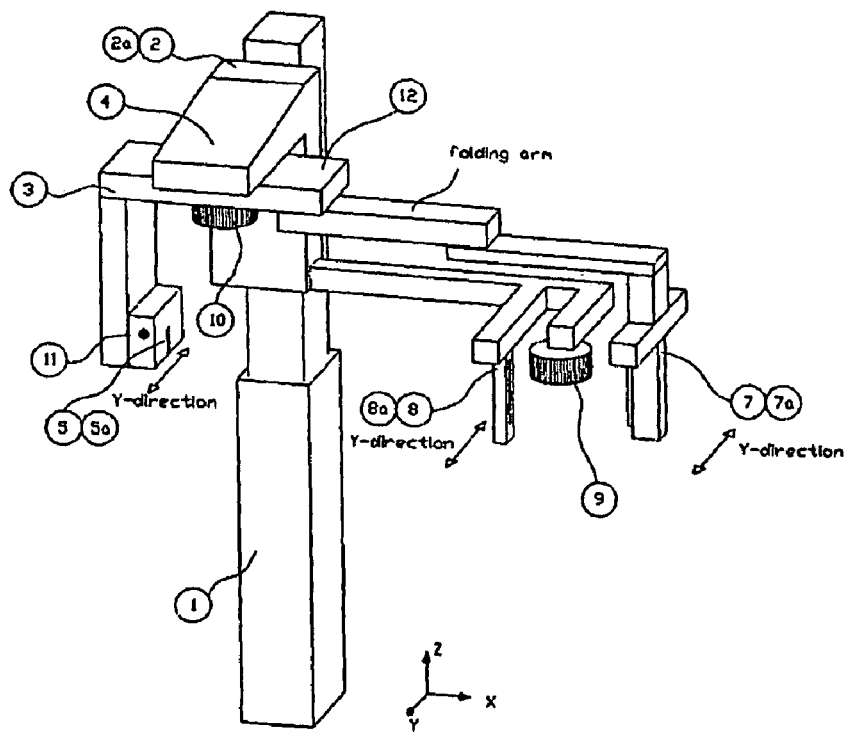

In FIG. 6D an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a, and 7a, under microcomputer control during the horizontal scanning sequence.

The secondary x-ray collimator 8 and the Cephalographic patient positioning system 9 are supported on an arm rigidly connected to the frame 2. An independent actuator 8a shall be foreseen providing movement of the secondary collimator 8 relative to the arm.

The x-ray imager 7 is relocated from Cephalographic to Panoramic position and vice versa by using a folding arm either provided with an active actuator 12 or to be manually actuated.

In FIG. 7, 7a, 7b, 7c arrangements are shown where the Real-Time Digital Cephalography is implemented by a scanning movement in the vertical direction of the Z-axis, using a narrow x-ray beam and a linear shaped x-ray imager having an active area of a length approximately corresponding to the minimum useful width of the x-ray field size at the film plane used in Conventional Cephalography.

In this arrangement a software post-processing of the acquired image will be required to correct the magnification distortion in the Z direction.

Figure 7:
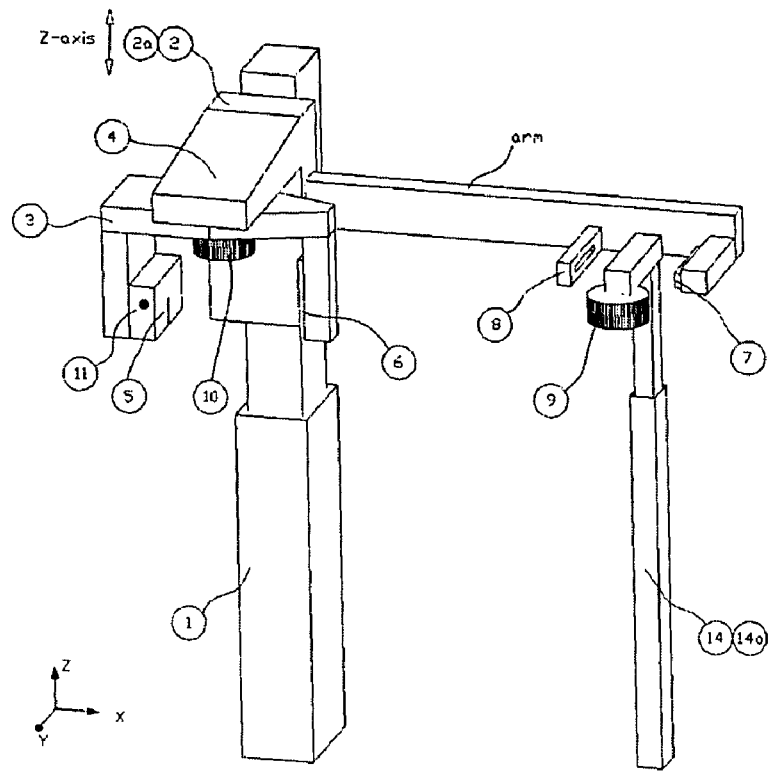

In FIG. 7 an arrangement is illustrated where the x-ray source 11, the primary x-ray collimator 5, the secondary x-ray collimator 8 and the x-ray imager 7 are simultaneously and linearly moved in the vertical direction, by acting on the Z axis under microcomputer control during the scanning sequence.

The Cephalographic patient positioning system 9 is rigidly connected to the base, to the wall, or to the floor (support 14), providing independent adjustment, either manual or motorized by the actuator 14a of the patient height.

Figure 7A:
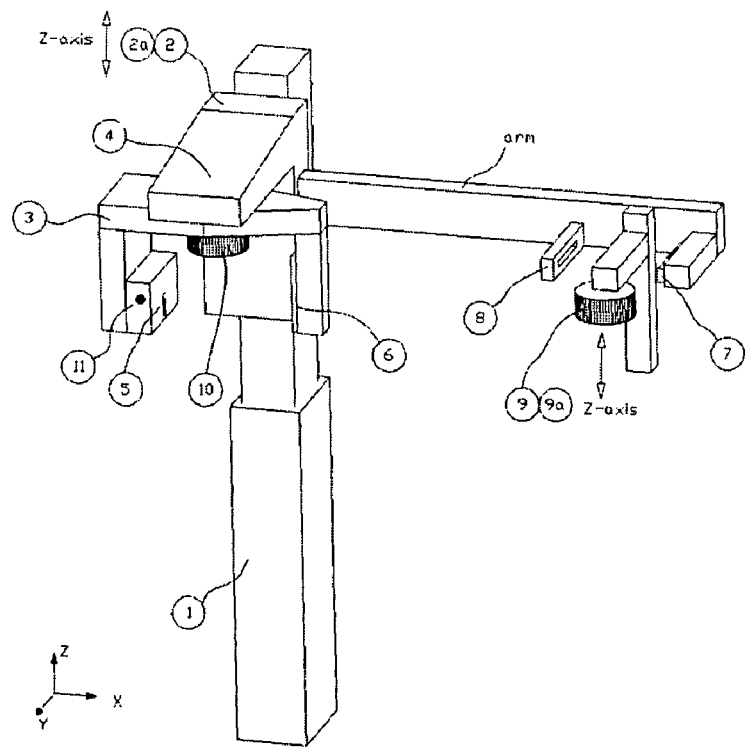

In FIG. 7a an arrangement is illustrated where the x-ray source 11, the primary x-ray collimator 5, the secondary x-ray collimator 8 and the x-ray imager 7 are simultaneously and linearly moved in the vertical direction, by acting on the Z axis under microcomputer control during the scanning sequence.

The Cephalographic patient positioning system 9 is supported on the same arm where the x-ray imager is suspended, where an independent active actuator 9a shall be foreseen providing movement relative to the supporting arm in opposition to the scanning movement, in order to maintain the patient in a firm position.

Figure 7B:
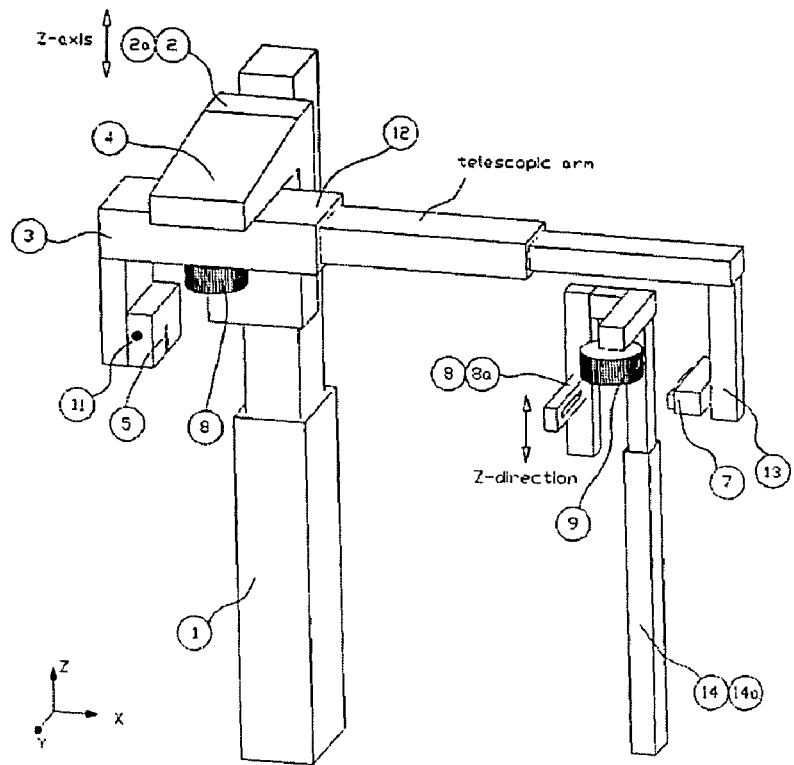
Figure 7C:
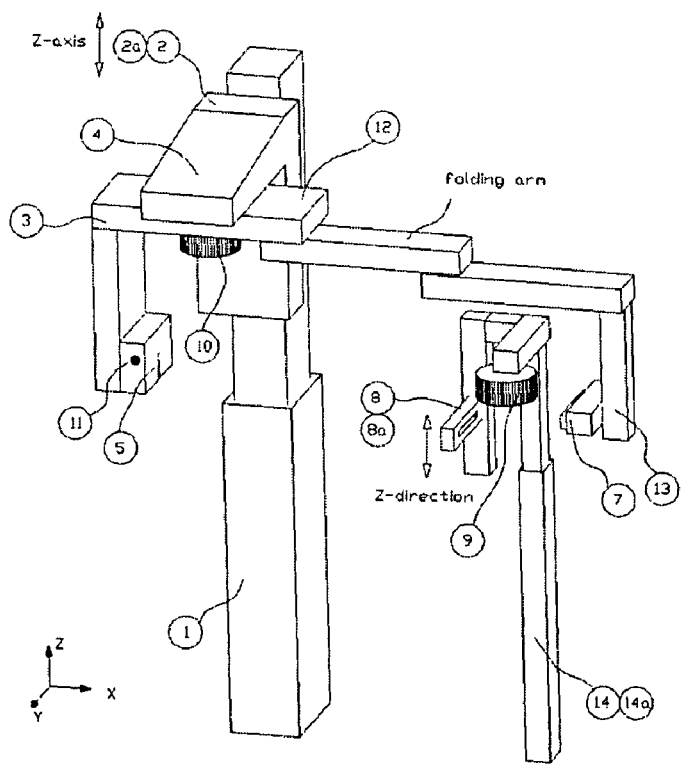

In the alternative arrangements of FIG. 7b, 7c, the x-ray imager 7 can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

In FIG. 7b an arrangement is shown, where the x-ray source 11, the primary x-ray collimator 5, and the x-ray imager 7 are simultaneously and linearly moved in the vertical direction, by acting on the Z axis under microcomputer control during the scanning sequence.

The Cephalographic patient positioning system 9 and the secondary x-ray collimator 8 are rigidly connected to the base, to the wall, or to the floor, by a support 14, providing independent adjustment of the patient height, either manual or motorized by the actuator 14a.

The secondary x-ray collimator 8 is synchronously moved, aligned with the x-ray beam, by the independent actuator 8a under microcomputer control during the scanning sequence.

The x-ray imager 7 is relocated from Cephalographic to Panoramic position and vice versa by using a telescopic arm either provided with an active actuator 12 or to be manually actuated. After relocation by the telescopic arm, the linear shaped imager is tilted in the horizontal position by an independent actuator 13.

In FIG. 7c an arrangement is shown, where the x-ray source 11, the primary x-ray collimator 5, and the x-ray imager 7 are simultaneously and linearly moved in the vertical direction, by acting on the Z axis under microcomputer control during the scanning sequence.

The Cephalographic patient positioning system 9 and the secondary x-ray collimator 8 are rigidly connected to the base, to the wall, or to the floor, by a support 14, providing independent adjustment of the patient height, either manual or motorized by the actuator 14a.

The secondary x-ray collimator 8 is synchronously moved, aligned with the x-ray beam, by the independent actuator 8a under microcomputer control during the scanning sequence.

The x-ray imager 7 is relocated from Cephalographic to Panoramic position and vice versa by using a folding arm either provided with an active actuator 12 or to be manually actuated. After relocation by the folding arm, the linear shaped imager is tilted in the horizontal position by an independent actuator 13.

In FIG. 8, 8a, 8b arrangements are shown where the Real-Time Digital Cephalography is implemented by a scanning movement in the vertical direction (Z-direction) of the primary x-ray collimator 5, using a narrow x-ray beam and a linear shaped x-ray imager having an active area of a length approximately corresponding to the minimum useful width of the x-ray field size at the film plane used in Conventional Cephalography.

In these arrangements no software post-processing of the acquired image will be required.

In FIG. 8 an arrangement is illustrated where the x-ray source 11 is kept steady, while the primary x-ray collimator 5, the secondary x-ray collimator 8 and the x-ray imager 7 are synchronously moved, aligned with the x-ray beam, by using their respective actuators 5a, 8a, 7a under microcomputer control during the vertical scanning sequence.

The Cephalographic patient positioning system 9 is supported on the same arm where the x-ray imager is suspended. The arm is rigidly connected to the frame 2.

In the alternative arrangements of FIG. 8a, 8b, the x-ray imager 7 can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

In FIG. 8a an arrangement is illustrated, where the x-ray source 11 is kept steady, while the primary x-ray collimator 5, the secondary x-ray collimator 8 and the x-ray imager 7 are synchronously moved, aligned with the x-ray beam, by using their respective actuators 5a, 8a, 7a under microcomputer control during the vertical scanning sequence.

The Cephalographic patient positioning system 9 and the secondary x-ray collimator 8 are rigidly connected to the base, to the wall, or to the floor by the support 14, providing independent adjustment of the patient height, either manual or motorized by the actuator 14a.

The independent actuator 8a provides movement of the secondary collimator 8 relative to the supporting arm.

The x-ray imager 7 can be relocated from Cephalographic to Panoramic position and vice versa by using a telescopic arm either provided with an active actuator 12 or to be manually actuated. After relocation by the telescopic arm, the linear shaped imager is tilted in the horizontal position by an independent actuator 13.

In FIG. 8b an arrangement is illustrated, where the x-ray source 11 is kept steady, while the primary x-ray collimator 5, the secondary x-ray collimator 8 and the x-ray imager 7 are synchronously moved, aligned with the x-ray beam, by using their respective actuators 5a, 8a, 7a under microcomputer control during the vertical scanning sequence.

The Cephalographic patient positioning system 9 and the secondary x-ray collimator 8 are rigidly connected to the base, to the wall, or to the floor by the support 14, providing independent adjustment of the patient height, either manual or motorized by the actuator 14a.

The independent actuator 8a provides movement of the secondary collimator 8 relative to the supporting arm.

The x-ray imager 7 can be relocated from Cephalographic to Panoramic position and vice versa by using a folding arm either provided with an active actuator 12 or to be manually actuated. After relocation by the folding arm, the linear shaped imager is tilted in the horizontal position by an independent actuator 13.

Figure 9:
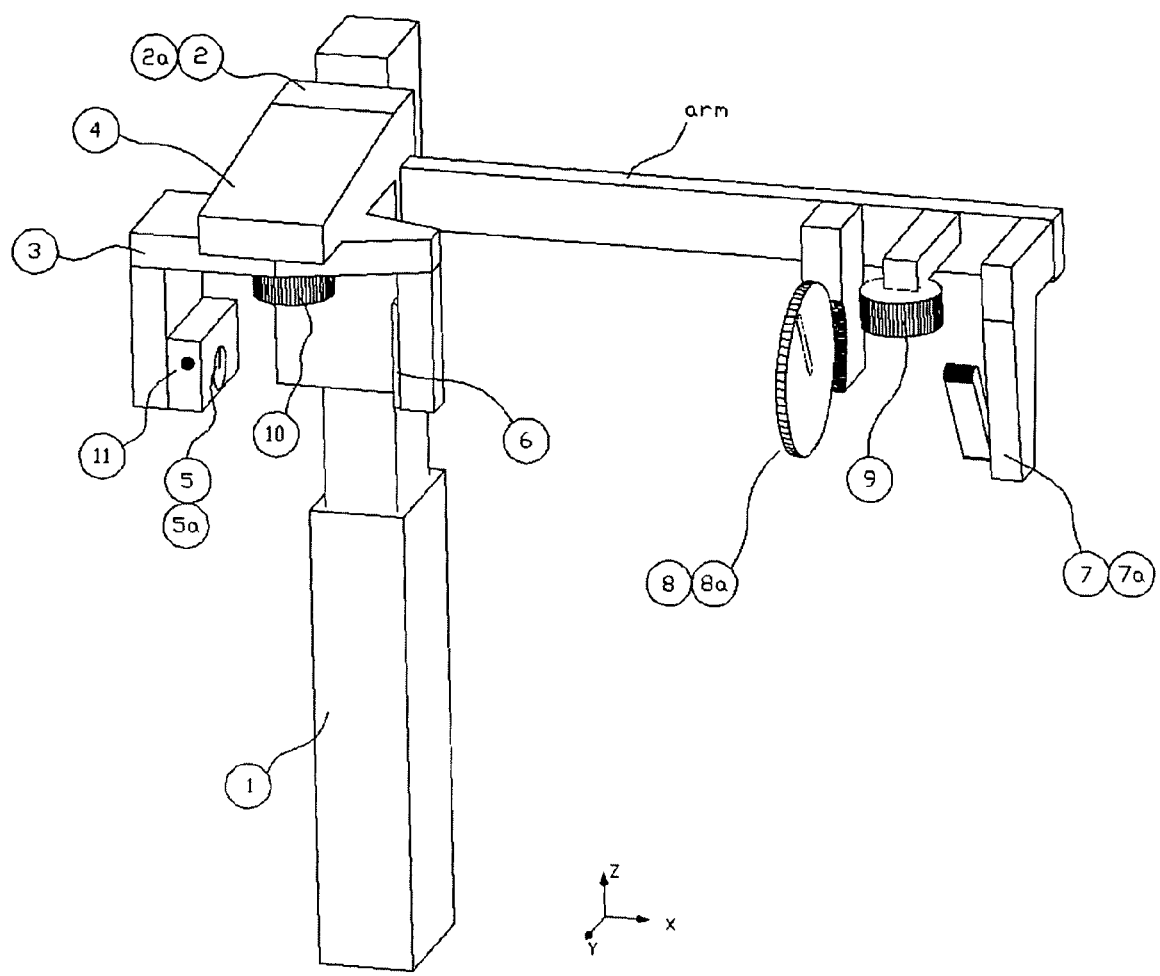
Figure 9A:
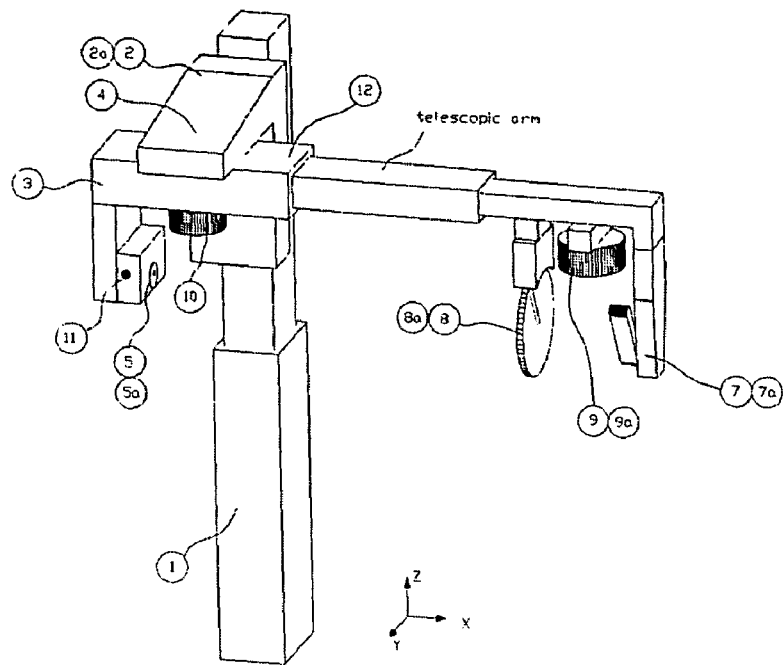
Figure 9B:
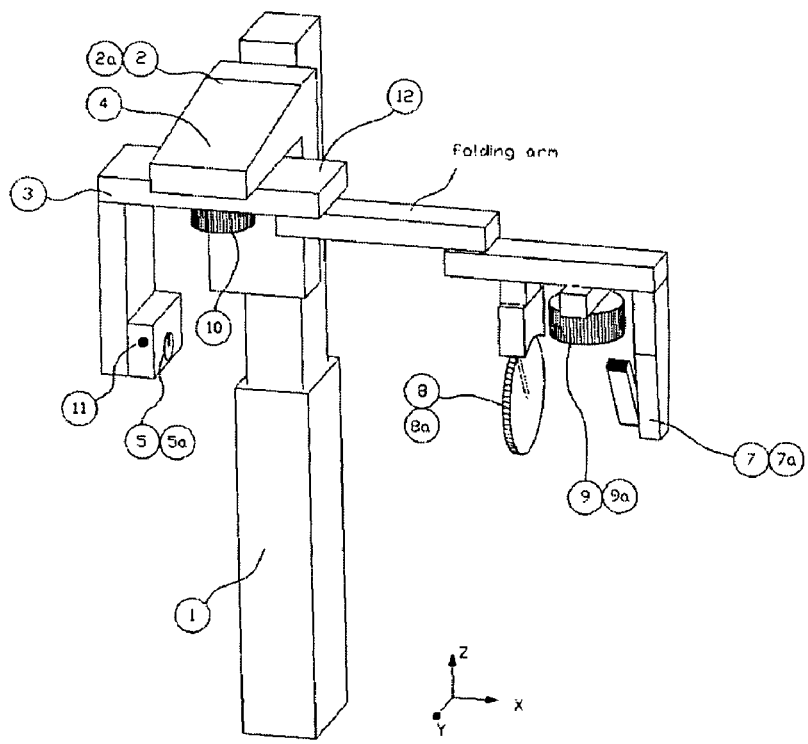

In FIG. 9, 9a, 9b arrangements are shown where the Real-Time Digital Cephalography is implemented by a rotatory scanning movement of the primary x-ray collimator 5, using a narrow x-ray beam and a linear shaped x-ray imager having an active area of a length approximately corresponding to half the minimum useful height of the x-ray field at the film plane.

In these arrangements software post-processing of the acquired image will be required, in order to perform geometric correction of the magnification distortions.

In FIG. 9 the arrangement is illustrated where the x-ray source 11 is kept steady, while the primary x-ray collimator 5, the secondary x-ray collimator 8 and the x-ray imager 7 are synchronously moved, aligned with the x-ray beam, by using their respective actuators 5a, 8a, 7a under microcomputer control during the rotational scanning sequence.

The Cephalographic patient positioning system 9 is supported on the same arm where the x-ray imager is suspended. The arm is rigidly connected to the frame 2.

In the alternative arrangements of FIG. 9a, 9b, 9C, 9D, the x-ray imager 7 can be relocated from Cephalography to Panoramic Radiography, Scannography and Linear Tomography. In this way the x-ray imager 7 takes the position and replaces the x-ray imager 6, so achieving a remarkable reduction of the system cost.

The extension movement of the apparatus may be automatically triggered and controlled by a user command or by the selection of the radiographic modality. It shall prevent collisions with the patient positioning system, and shall incorporate provision for safety release to avoid potential injury to the patient.

In FIG. 9a the arrangement is illustrated where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a and 7a, under microcomputer control during the rotational scanning sequence.

The Cephalographic patient positioning system 9 is supported on the same arm where the x-ray imager 7 is suspended and is kept steady during the scanning process.

The x-ray imager 7 can be relocated from Cephalographic to Panoramic position and vice versa by using a telescopic arm either provided with an active actuator 12 or to be manually actuated.

In FIG. 9b the arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a and 7a, under microcomputer control during the rotational scanning sequence.

The Cephalographic patient positioning system 9 is supported on the same arm where the x-ray imager is suspended and is kept steady during the scanning process.

The x-ray imager 7 can be relocated from Cephalographic to Panoramic position and vice versa by using a folding arm either provided with an active actuator 12 or to be manually actuated.

Figure 9C:
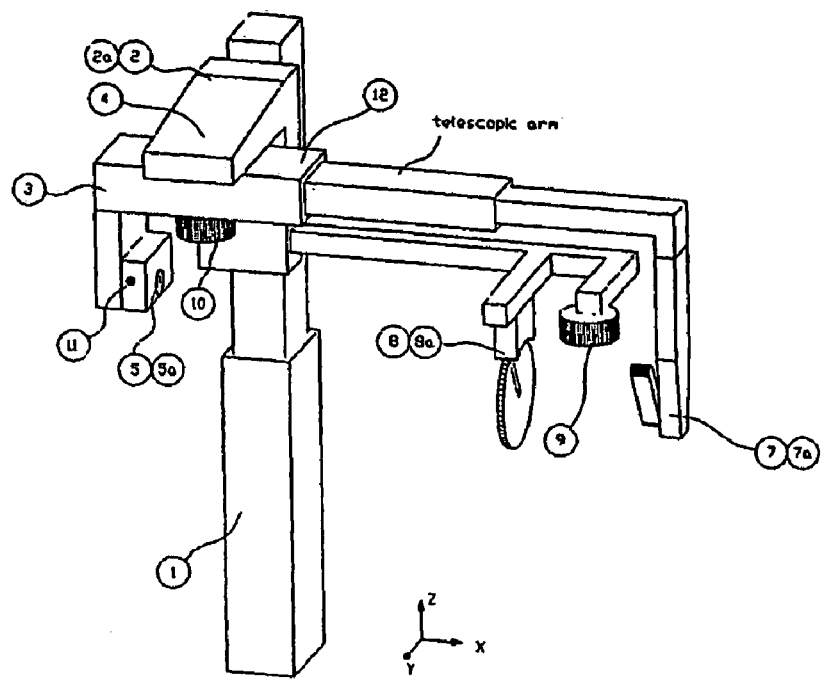

In FIG. 9C an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a, and 7a, under microcomputer control during the rotational scanning sequence.

The secondary x-ray collimator 8 and the Cephalographic patient positioning system 9 are supported on an arm rigidly connected to the frame 2.

The x-ray imager 7 can be relocated from Cephalographic to Panoramic position and vice versa by using a telescopic arm either provided with an active actuator 12 or to be manually actuated.

Figure 9D:
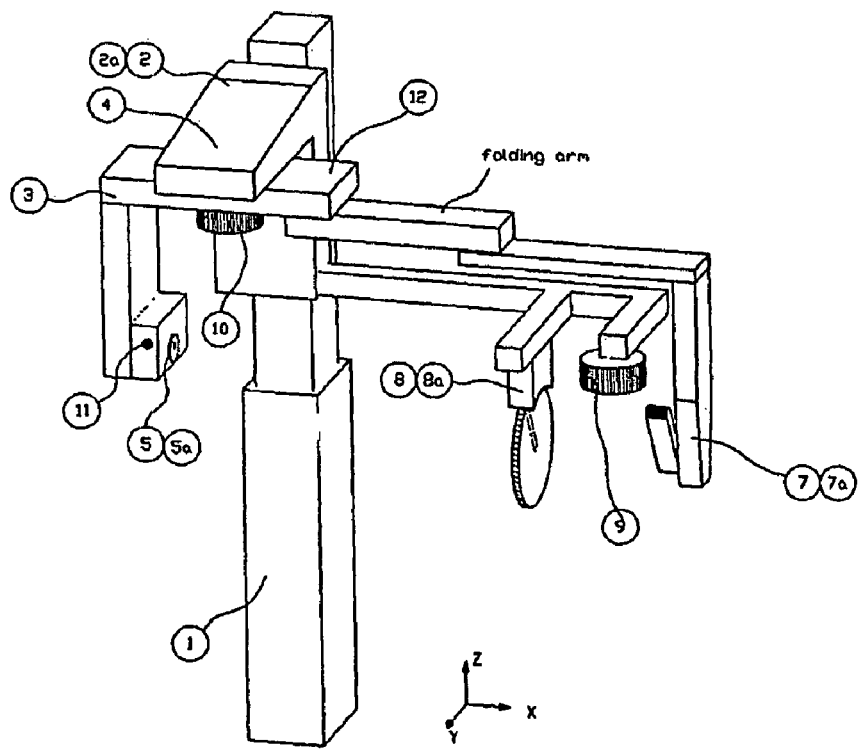

In FIG. 9D an arrangement is illustrated, where the x-ray source 11 is kept steady, while the primary x-ray collimator 5, the secondary x-ray collimator 8 and the x-ray imager 7 are synchronously moved, aligned with the x-ray beam, by using the respective drive axis, 5a, 8a, and 7a, under microcomputer control during the rotational scanning sequence.

The secondary x-ray collimator 8 and the Cephalographic patient positioning system 9 are supported on an arm rigidly connected to the frame 2.

The x-ray imager 7 is relocated from Cephalographic to Panoramic position and vice versa by using a folding arm either provided with an active actuator 12 or to be manually actuated.

In FIG. 10 an arrangement is shown where a detachable connector 100 allows, in a secure and ergonomic way, the manual connection and disconnection of the x-ray imager 6 selectively between the Cephalographic and the Panoramic position.

We claim:

1. A dental x-ray diagnostic apparatus for performing real-time digital radiography in Cephalography of a patient skull, the apparatus comprising:
   a base frame arrangement;
   a rotary frame coupled to the base frame arrangement, the rotary frame supporting an x-ray source;
   a cinematic unit connecting the rotary frame and the base frame arrangement, the cinematic unit being configured to execute roto-translational movements of the rotary frame, wherein the roto-translational movements comprise one rotation movement and two transverse linear movements in a horizontal plane, and the roto-translational movements of the rotary frame being driven by independent actuators in the cinematic unit controlled by data supplied from a microcomputer;
   an x-ray imager disposed in a Cephalographic position, the x-ray imager being movable during a scanning operation by an independent actuator; and
   wherein the roto-translational movements of the cinematic unit permit the rotary frame to perform a roto-translating scanning trajectory to permit illumination of the patient skull by the x-ray source from a predefined virtual center of irradiation.

2. An apparatus as in claim 1, further comprising a second x-ray imager, the second x-ray imager being supported by the rotary frame and disposed opposite the x-ray source in a Panoramic position.

3. The apparatus as set forth in claim 2 wherein the second x-ray imager has an active area of a size approximately equivalent to a radiographic film.

4. The apparatus as set forth in claim 1 wherein the predefined virtual center of irradiation is located at the focal point of the x-ray source.

5. The apparatus as set forth in claim 1 wherein said x-ray imager is associated with a horizontal scanning movement, and has a linearly shaped active area oriented vertically with a height substantially greater than a width.

6. The apparatus as set forth in claim 1 wherein said x-ray imager is associated with a horizontal scanning movement, and is linearly translated during a scanning movement by computer control of the independent actuator for the x-ray imager.

7. The apparatus as set forth in claim 1 wherein said x-ray imager is associated with a vertical scanning movement, and has a linearly shaped active area oriented horizontally with a width substantially greater than a height.

8. The apparatus as set forth in claim 1 wherein said x-ray imager is associated with a rotational scanning movement, and has a linearly shaped active area for use with a narrow x-ray beam.

9. The apparatus as set forth in claim 1 wherein said x-ray imager is associated with a vertical, or horizontal, or rotational scanning movement, and an x-ray beam is collimated by a collimator intercepting the x-ray beam before a patient and in proximity of the patient, which is provided with an independent active actuator capable of performing the linear or rotational translation of the collimator during a scanning movement under computer control.

10. The apparatus as set forth in claim 1, comprising a collimator operated by independent active actuators under microcomputer control, allowing resizing of an x-ray field to any desired format required for a chosen radiographic modality as well as a translation of the x-ray field during a vertical or horizontal or rotational scanning process.

11. The apparatus as set forth in claim 1 wherein a mechanism is given providing relocation of said x-ray imager selectively between a Cephalographic and a Panoramic position.

12. The apparatus as set forth in claim 11 wherein such mechanism comprises a telescopic arm providing relocation either manually or automatically by an independent actuator under microcomputer control upon user command.

13. The apparatus as set forth in claim 11 wherein such mechanism comprises a folding arm providing relocation either manually or automatically by an independent actuator under microcomputer control upon user command.

14. The apparatus as set forth in claim 11 wherein such mechanism comprises a detachable connector allowing in a secure and ergonomic way the manual connection and disconnection of the x-ray imager selectively between the Cephalographic and the Panoramic position.

15. The apparatus as set forth in claim 1 wherein a patient positioning system used in Cephalography is provided with independent active actuators by which the patient positioning system can be translated relative to a corresponding support frame in order to maintain a firm patient position during a horizontal or vertical scanning process where a movement of the support frame is involved.

16. A method for operating a dental x-ray diagnostic apparatus performing real-time digital radiography in Cephalography, comprising the steps of:
    positioning a patient by a patient positioning system;
    irradiating a patient skull from a predefined virtual center of irradiation of an x-ray source during a roto-translational movement of a rotary frame supporting the x-ray source and a linear movement of an x-ray imager positioned in a Cephalographic position;
    performing acquisition of image data by the x-ray imager and digital processing of the image data for reconstruction of a diagnostic image; and
    wherein the roto-translational movements of the rotary frame include one rotational movement and two transverse linear movements in a horizontal plane, and the roto-translational movements of the rotary frame being driven by independent actuators in the cinematic unit controlled by data supplied from a microcomputer.

17. A method for operating a dental x-ray diagnostic apparatus performing real-time digital radiography in cephalography, comprising the steps of:
    aligning an x-ray source with an x-ray imager, either manually or automatically;
    positioning a patient by a patient positioning system;
    setting a collimator to provide a narrow x-ray beam;
    starting a scanning process during which the x-ray beam is rotationally translated about a horizontal axis through a patient skull by a coordinated rotational movement of the collimator and the x-ray imager under computer control, while the x-ray source is fixed in position; and
    performing acquisition of image data by the x-ray imager, and computer processing for reconstruction of a diagnostic image.

* * * * *

UNITED STATES PATENT AND TRADEMARK OFFICE
CERTIFICATE OF CORRECTION

PATENT NO.       : 7,197,109 B2                                     Page 1 of 1
APPLICATION NO.  : 10/623833
DATED            : March 27, 2007
INVENTOR(S)      : Rotondo et al.

It is certified that error appears in the above-identified patent and that said Letters Patent is hereby corrected as shown below:

On the Title Page, Item [56], under References Cited - U.S. PATENT DOCUMENTS, insert the following U.S. Patents:

--5,371,775 A  12/1994  Kanerva et al.
  5,436,950 A  07/1995  Pauli et al.
  5,469,429 A  11/1995  Yamazaki et al.
  5,590,164 A  12/1996  Kawai et al.
  5,666,392 A  09/1997  Ploetz et al.
  5,921,927 A  07/1999  McArdle
  6,009,147 A  12/1999  Stein et al.--

Signed and Sealed this

Nineteenth Day of October, 2010

David J. Kappos
*Director of the United States Patent and Trademark Office*